(12) United States Patent
Sethna et al.

(10) Patent No.: US 8,751,018 B1
(45) Date of Patent: Jun. 10, 2014

(54) IMPLANTABLE LEAD AND METHOD OF MAKING THE SAME

(75) Inventors: Dorab N. Sethna, Valencia, CA (US);
Keith Victorine, Studio City, CA (US);
Scott Salys, Los Angeles, CA (US)

(73) Assignee: Pacesetter Inc., Sylmar, CA (US)

( * ) Notice: Subject to any disclaimer, the term of this patent is extended or adjusted under 35 U.S.C. 154(b) by 516 days.

(21) Appl. No.: 11/855,064

(22) Filed: Sep. 13, 2007

Related U.S. Application Data

(63) Continuation-in-part of application No. 11/745,728, filed on May 8, 2007, now abandoned.

(51) Int. Cl.
*A61N 1/05* (2006.01)

(52) U.S. Cl.
USPC .................................................... 607/119

(58) Field of Classification Search
USPC ................................. 600/374; 607/119–132
See application file for complete search history.

(56) References Cited

U.S. PATENT DOCUMENTS

| | | | |
|---|---|---|---|
| 4,627,439 A * | 12/1986 | Harris | 166/272.5 |
| 4,815,469 A | 3/1989 | Cohen et al. | |
| 4,934,049 A * | 6/1990 | Kiekhafer et al. | 29/883 |
| 5,005,587 A | 4/1991 | Scott | |
| 5,042,143 A * | 8/1991 | Holleman et al. | 29/825 |
| 5,063,018 A | 11/1991 | Fontirroche et al. | |
| 5,115,818 A * | 5/1992 | Holleman et al. | 607/122 |
| 5,387,233 A * | 2/1995 | Alferness et al. | 607/126 |
| 5,527,325 A | 6/1996 | Conley et al. | |
| 5,662,606 A | 9/1997 | Cimino et al. | |
| 5,713,851 A | 2/1998 | Boudewijn et al. | |
| 5,792,401 A | 8/1998 | Burnham | |
| 5,796,044 A | 8/1998 | Cobian et al. | |
| 5,879,499 A | 3/1999 | Corvi | |
| 5,935,159 A | 8/1999 | Cross, Jr. et al. | |
| 5,999,858 A | 12/1999 | Sommer et al. | |
| 6,249,708 B1 | 6/2001 | Nelson et al. | |
| 6,623,480 B1 | 9/2003 | Kuo et al. | |
| 6,721,604 B1 | 4/2004 | Robinson et al. | |
| 6,757,970 B1 | 7/2004 | Kuzma et al. | |
| 6,827,798 B1 | 12/2004 | Ichikawa et al. | |
| 6,852,946 B2 * | 2/2005 | Groen et al. | 219/121.68 |
| 6,945,956 B2 * | 9/2005 | Waldhauser et al. | 604/95.01 |
| 7,353,066 B1 | 4/2008 | Chitre et al. | |
| 7,641,757 B2 | 1/2010 | Kampa et al. | |
| 2001/0015253 A1 | 8/2001 | Liska et al. | |
| 2002/0147486 A1 * | 10/2002 | Soukup et al. | 607/122 |

(Continued)

OTHER PUBLICATIONS

Advisory Action, mailed Apr. 22, 2008: Related U.S. Appl. No. 11/330,501.

(Continued)

*Primary Examiner* — Carl H Layno
*Assistant Examiner* — Erica Lee

(57) ABSTRACT

A method of manufacturing an implantable lead includes providing a core including at least one longitudinal lumen; providing a jacket comprising a reflowable material; positioning the core at least partially within the jacket; and, after positioning, applying heat to cause the material of the jacket to reflow and bond to the core. An implantable lead includes a core including at least one longitudinal lumen; and a jacket comprising a reflowable material. The core may be at least partially disposed within the jacket with the material of the jacket reflow-bonded to the core. The implantable lead may further include at least one lead component associated with at least one of the core and the jacket.

24 Claims, 25 Drawing Sheets

(56) References Cited

U.S. PATENT DOCUMENTS

| | | | |
|---|---|---|---|
| 2002/0188326 | A1 | 12/2002 | Zheng et al. |
| 2003/0050681 | A1* | 3/2003 | Pianca et al. .................. 607/125 |
| 2003/0065364 | A1 | 4/2003 | Wellman et al. |
| 2004/0020549 | A1* | 2/2004 | Augscheller et al. ..... 139/383 A |
| 2004/0039369 | A1 | 2/2004 | Shelso |
| 2004/0054349 | A1 | 3/2004 | Brightbill |
| 2004/0064086 | A1 | 4/2004 | Gottlieb et al. |
| 2004/0068240 | A1 | 4/2004 | Goodin et al. |
| 2004/0073158 | A1 | 4/2004 | Shah et al. |
| 2004/0097965 | A1 | 5/2004 | Gardeski et al. |
| 2004/0116993 | A1 | 6/2004 | Clemens et al. |
| 2005/0203604 | A1 | 9/2005 | Brabec et al. |
| 2005/0222659 | A1* | 10/2005 | Olsen et al. ................... 607/116 |
| 2006/0041293 | A1 | 2/2006 | Mehdizadeh et al. |
| 2008/0161774 | A1 | 7/2008 | Hastings et al. |
| 2008/0183265 | A1* | 7/2008 | Bly et al. ....................... 607/122 |

OTHER PUBLICATIONS

NonFinal Office Action, mailed Feb. 25, 2009: Related U.S. Appl. No. 12/144,547.
NonFinal Office Action, mailed May 12, 2009: Related U.S. Appl. No. 11/745,728.
NonFinal Office Action, mailed May 12, 2009: Related U.S. Appl. No. 11/745,705.
NonFinal Office Action, mailed Jul. 9, 2007: Related U.S. Appl. No. 11/330,501.
Final Office Action, mailed Dec. 31, 2007: Related U.S. Appl. No. 11/330,501.
Notice of Allowance, mailed Nov. 9, 2009—Related U.S. Appl. No. 12/144,547.
NonFinal Office Action, mailed May 12, 2009—Related U.S. Appl. No. 11/745,705.
NonFinal Office Action, mailed Oct. 29, 2009—Related U.S. Appl. No. 11/745,705.
NonFinal Office Action, mailed Oct. 27, 2009—Related U.S. Appl. No. 11/745,728.
Final Office Action, mailed Apr. 26, 2010—Related U.S. Appl. No. 11/745,728.
Final Office Action, mailed Apr. 19, 2010—Related U.S. Appl. No. 11/745,705.
NonFinal Office Action, mailed Jan. 3, 2011—Related U.S. Appl. No. 11/745,705.
Final Office Action, mailed Jun. 22, 2011—Related U.S. Appl. No. 11/745,705.
Advisory Action, mailed Jun. 28, 2010—Related U.S. Appl. No. 11/745,728.
Advisory Action, mailed Jun. 28, 2010—Related U.S. Appl. No. 11/745,705.

* cited by examiner

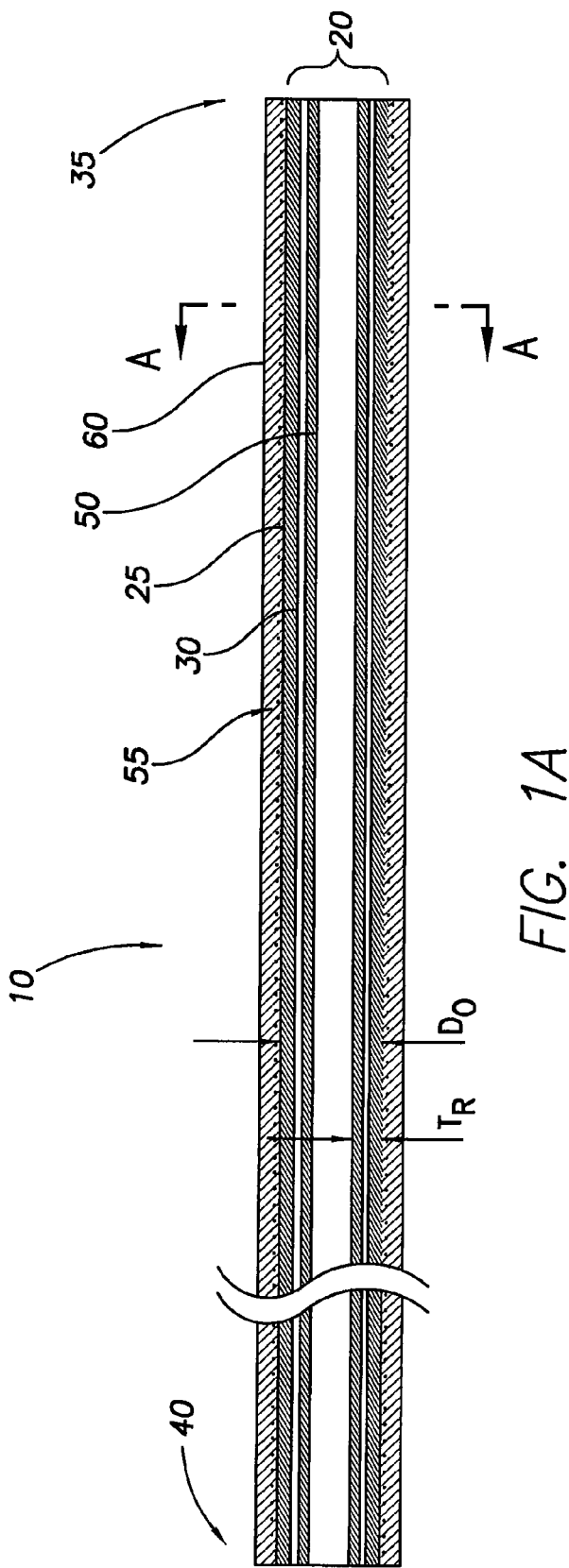
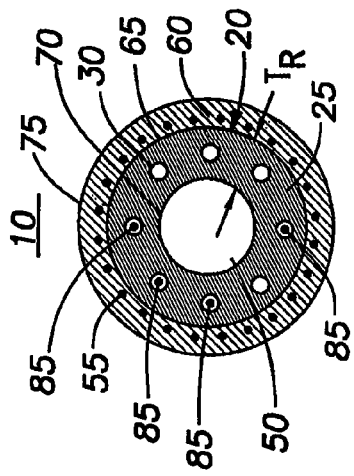
FIG. 1A
FIG. 1B

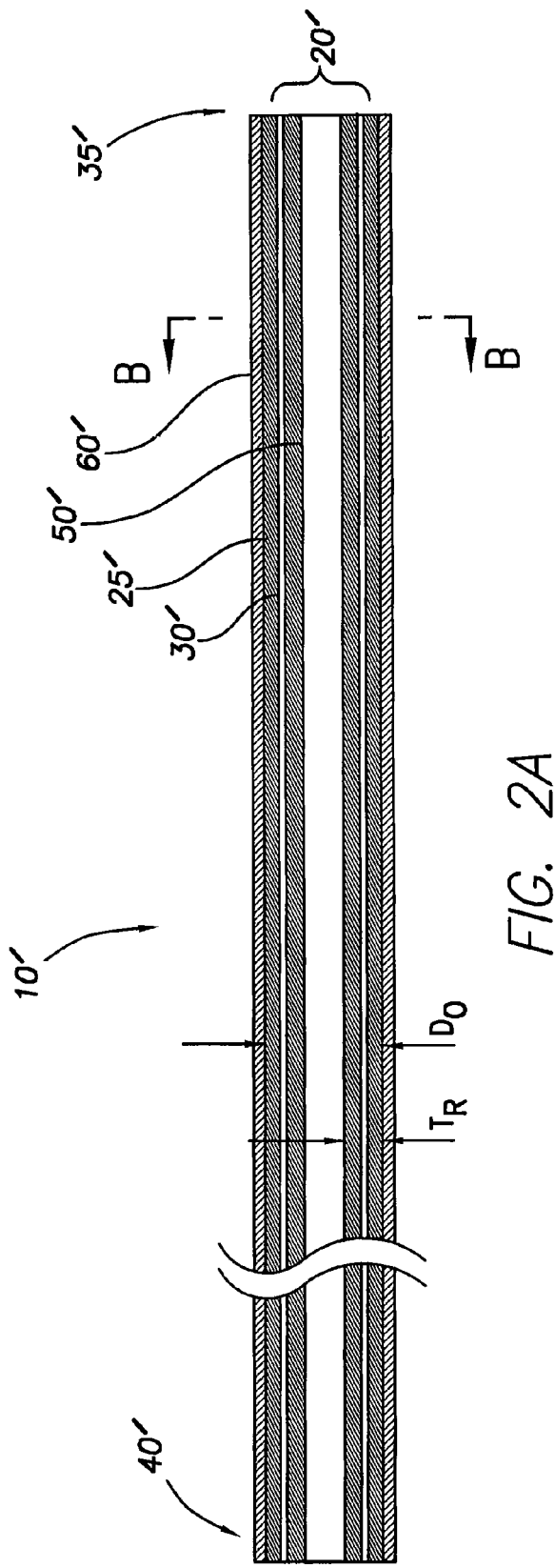
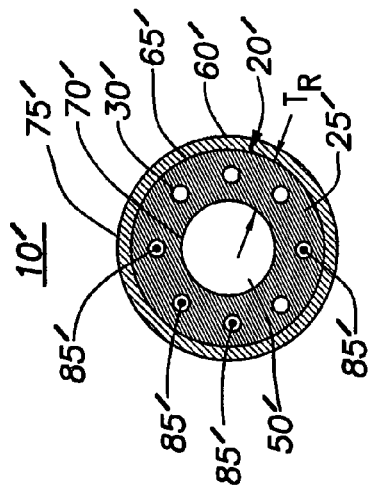
FIG. 2A
FIG. 2B

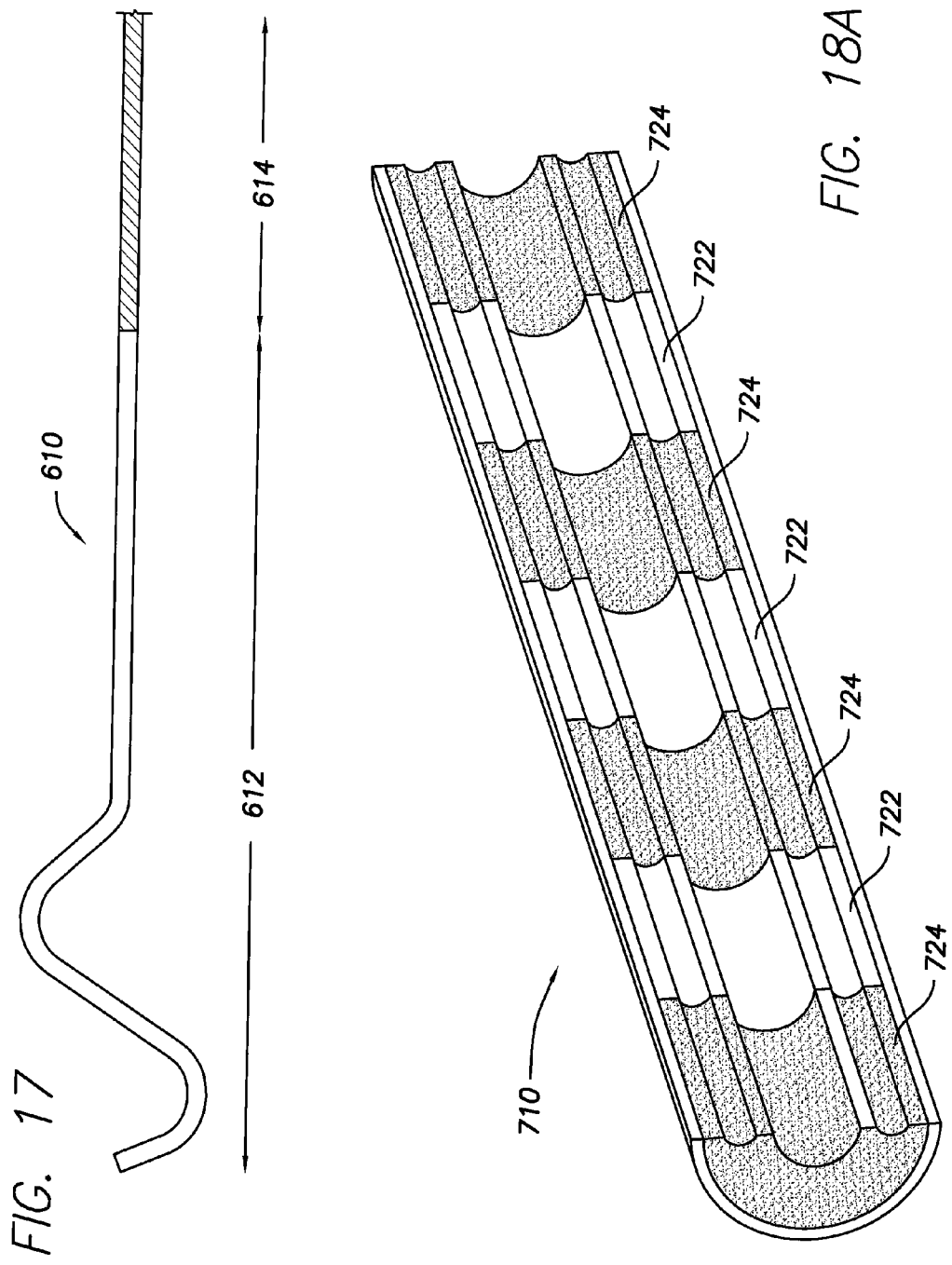

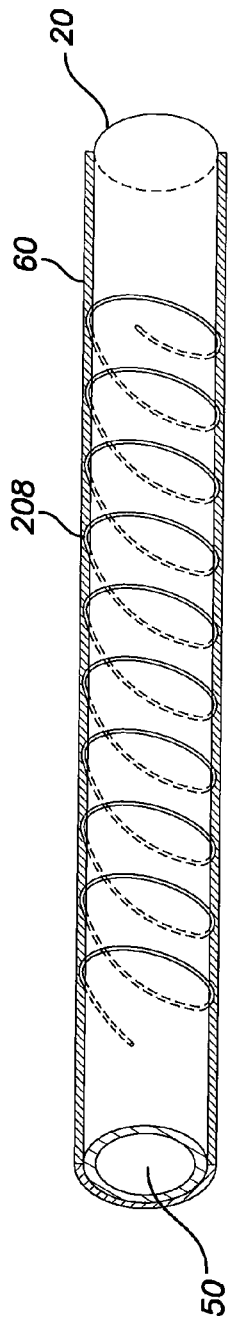
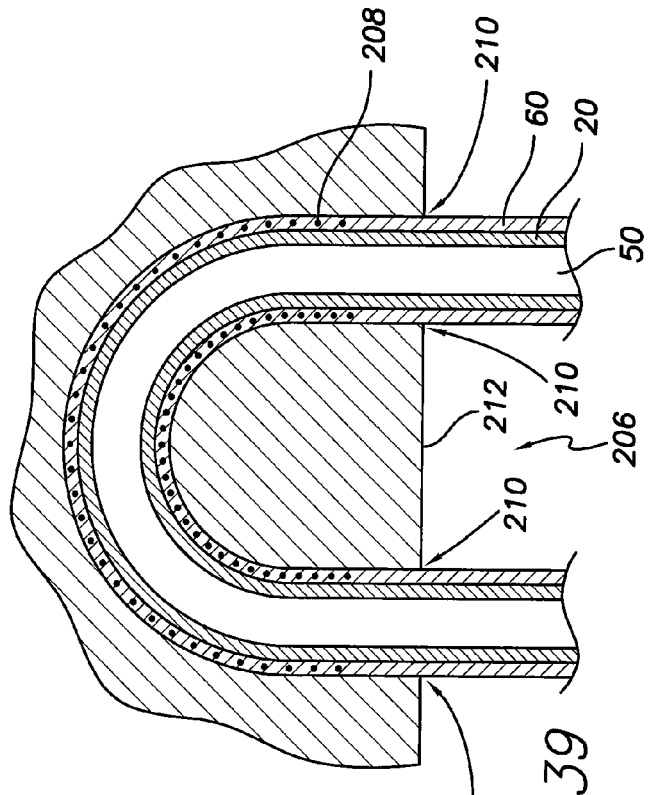
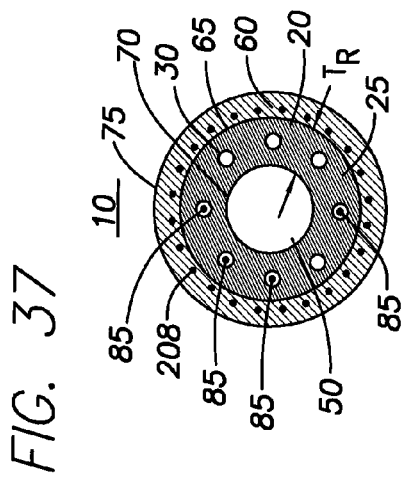
FIG. 38
FIG. 39
FIG. 37

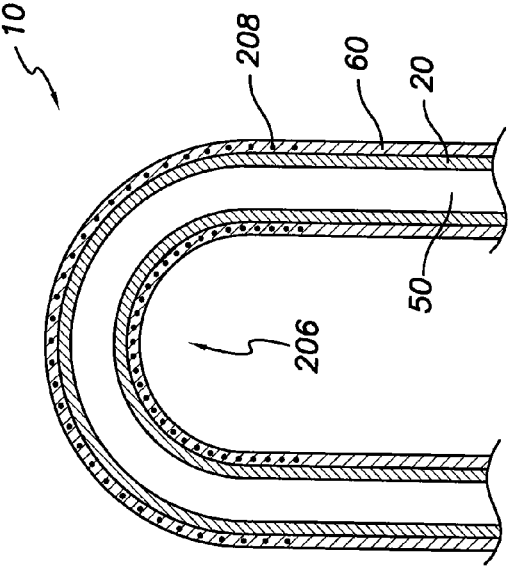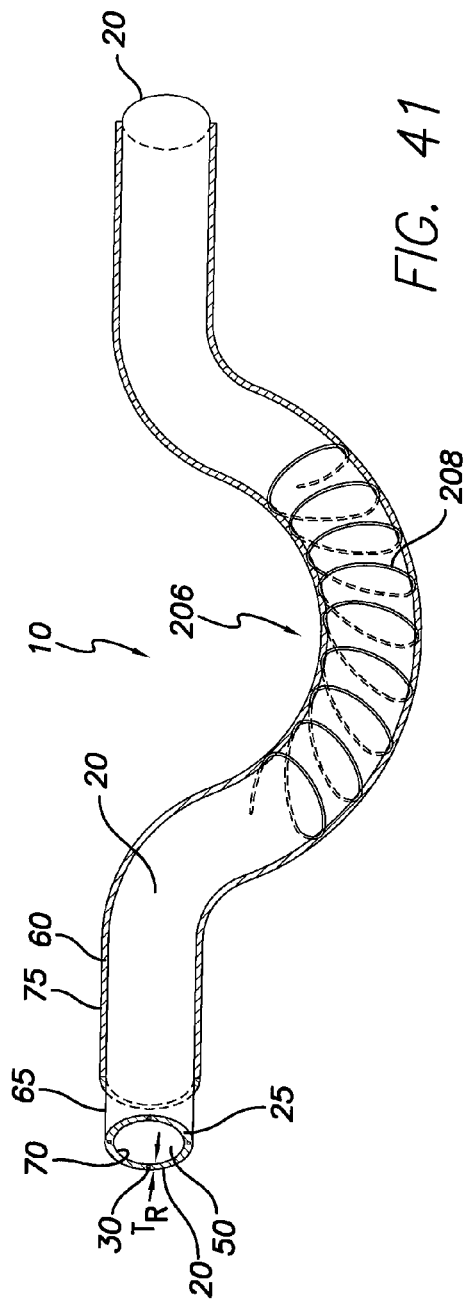

IMPLANTABLE LEAD AND METHOD OF MAKING THE SAME

CROSS-REFERENCE TO RELATED APPLICATIONS

The present application is a continuation-in-part ("CIP") of U.S. patent application Ser. No. 11/745,728, filed May 8, 2007, entitled "Implantable Lead and Method of Making Same now abandoned"; and is related to U.S. patent application Ser. No. 11/745,705, filed May 8, 2007, entitled "Implantable Lead and Method of Making the Same now abandoned." The aforementioned applications are incorporated by reference into the present application in their entireties.

FIELD OF THE INVENTION

The present invention relates to medical devices and methods. More specifically, the present invention relates to implantable leads and methods of making such implantable leads.

BACKGROUND OF THE INVENTION

Implantable cardiac devices have become increasingly sophisticated and more capable over time. Similarly, implantable leads for such cardiac devices and neural stimulation have also become increasingly sophisticated and more capable over time. Various enhancements and various manufacturing techniques for achieving such enhancements have been developed.

For example, known manufacturing techniques include extrusion, bonding and molding. Various components such as cores and sheaths may be made by extruding materials. Various components such as conductors and electrodes may be bonded to form a desired structural arrangement.

Conventional technology for manufacturing implantable leads has essentially reached a limit in the ability to adjust to rapid changes in customer needs and to incorporate enhancements in a timely fashion. For example, conventional bonding techniques involve multiple bonding operations that are carried out independently. Each bonding operation has an associated cure time, as well as pre-processing and post-processing times. Conventional extrusion techniques are limited, for example, with respect to downsizing of implantable leads because of the need for clearance between mating parts. Conventional extrusion techniques also do not allow for novel components or devices to be easily incorporated into implantable leads.

Thus, there is a need in the art for an improved method for manufacturing implantable leads. There is also a need in the art for implantable leads that include enhanced features and/or characteristics.

BRIEF SUMMARY OF THE INVENTION

Embodiments of the present invention contemplate a platform upon which implantable leads may be manufactured. Specifically, embodiments of the invention contemplate using reflow technology to manufacture implantable leads. Such an approach may simplify the incorporation of components and/or enhancements to basic lead architectures. Such an approach may increase the versatility and flexibility of implantable leads and their manufacture. In particular, such an approach may provide adaptability for rapid design changes to meet industry changes and/or customer needs.

The present invention relates to a method of manufacturing an implantable lead. The method may include providing a core including at least one longitudinal lumen; providing an extruded jacket comprising a reflowable material; positioning the core at least partially within the jacket; and, after positioning, applying heat to cause the material of the jacket to reflow and bond to the core. The method may further comprise incorporating at least one lead component.

The present invention also relates to an implantable lead. The implantable lead may include a core including at least one longitudinal lumen; and an extruded jacket comprising a reflowable material; wherein the core is at least partially disposed within the jacket with the material of the jacket reflow-bonded to the core. The implantable lead may further include at least one lead component.

The present invention relates to methods of manufacturing an implantable lead. The method may include: providing a core including at least one longitudinal lumen; providing a coil about an outer circumferential surface of the core; providing a jacket about the coil, wherein the jacket is formed of a reflowable material; and causing the material of the jacket to reflow and bond to the core.

The present invention relates to an implantable lead. The lead may include a core, a first coil and a jacket. The core may include at least one lumen extending there through. The first coil may extend about an outer circumferential surface of the core. The jacket may be reflowed about the outer circumferential surface of the core, such that it impregnates the first coil.

While multiple embodiments are disclosed, still other embodiments of the present invention will become apparent to those skilled in the art form the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1A is a longitudinal sectional view of an embodiment of an implantable lead including a reinforcing structure.

FIG. 1B is a cross-sectional view of the implantable lead of FIG. 1A, taken along section line A-A.

FIG. 2A is a longitudinal sectional view of another embodiment of an implantable lead without a reinforcing structure.

FIG. 2B is a cross-sectional view of the implantable lead of FIG. 2A, taken along section line B-B.

FIG. 17 is a longitudinal view of an embodiment of an implantable lead including a composite core.

FIG. 18A is an isometric view of a partial longitudinal section of an embodiment of an implantable lead including a sectioned composite core.

FIG. 37 illustrates the lead in transverse cross-section after the removal of the heat-shrink tube.

FIG. 38 is an isometric view of a longitudinal segment of the lead in the same state depicted in FIG. 37, wherein the lead outer jacket is shown as a longitudinal cross-section to reveal the core and coil underneath.

FIG. 39 is a longitudinal cross-section of the lead in a curved forming fixture that has a curved channel for receiving therein the lead.

FIG. 40 is the same view as FIG. 39, except the lead has been removed from the curved channel of the forming fixture and the lead has the pre-shaped curve.

FIG. 41 is an isometric view of a longitudinal segment of the lead having the pre-shaped curve and wherein the lead outer jacket is shown as a longitudinal cross-section to reveal the core and coil underneath.

DETAILED DESCRIPTION

Figure 3:
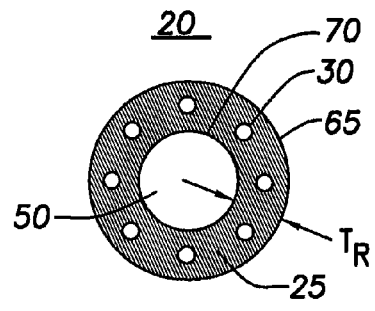
FIGS. 3-8 illustrate various stages of manufacture for the implantable lead of FIGS. 1A-B, in cross-section.

The present invention, in one embodiment, is an implantable lead 10 and a method of manufacturing the implantable lead. The implantable lead 10 may include a longitudinally extending core 20 and a jacket 60 of a reflowable material. The jacket 60 at least partially surrounds the core 20 and may be reflowed to bond to the core.

The implantable lead 10 may provide improved operability and decreased manufacturing costs. Also, the configuration and the method of manufacturing the lead 10 may provide a highly adaptable platform for designing implantable leads to meet a variety of needs.

For a discussion of the implantable lead, reference is made to FIGS. 1A-B. FIG. 1A is a longitudinal sectional view of the implantable lead 10, wherein the implantable lead is reinforced with a reinforcing structure 55. FIG. 1B is a cross-sectional view of the implantable lead 10 of FIG. 1A, taken along section line A-A in FIG. 1A.

As shown in FIG. 1A, the implantable lead 10 includes a distal end 35 for entering into a patient and a proximal end 40 for manipulation by a physician. In one embodiment, the implantable lead 10 includes the core 20, the reinforcing structure 55, and the outer jacket 60.

The core 20 may comprise a polymer material, such as a thermoset material. In particular, PTFE (polytetrafluoroethylene), ePTFE (expanded-polytetrafluoroethylene), silicone rubber, or a combination of such materials, may be used for the core 20. The jacket 60 may comprise an extruded material, such as a thermoplastic material. In particular, materials such as polyurethane, OPTIM™ (ElastEon 2A), ElastEon 5, CARBOSIL™ (silicone polycarbonate urethane), PEBAX® (polyether block amides), PIBS (polystyrene-b-polyisobutylene-b-polystyrene), etc. may be used for the jacket 60. In general, any suitable desired materials may be used for the core 20 and the jacket 60, as long as the jacket is reflowable at a temperature at which the core is unaffected.

As shown in FIGS. 1A-B, the polymer core 20 may include a central lumen 50, a circumferentially continuous core wall 25 with an outer diameter $D_O$, and one or more core wall lumens 30 longitudinally extending within the radial thickness $T_R$ of the core wall 25. The core wall 25 may include an outer circumferential surface 65 and an inner circumferential surface 70 that defines the central lumen 50.

The core wall lumens 30 may provide space for various lead components, including functional components, (e.g., conductor wires and/or electrodes for transmitting an electrical current for medical condition diagnosis and/or treatment, stylets, guide-wires or other delivery tools, shaped wires, crimp-slugs, deflection wires for deflecting a portion of the lead for implantation or fixation purposes, etc.) to be positioned or introduced.

The central lumen 50 may be open for the introduction of medical devices (e.g., stylets, guidewires, etc.) into the central lumen 50 by the physician. The central lumen 50 may be lined with a polymer liner formed of, for example, PTFE to facilitate the passage of devices through the central lumen 50 and reduce the likelihood of the devices piercing the central lumen 50. Alternatively, the central lumen 50 may be lined with a coil, which may be a single or multi-filar helically wound coil. The filars may have circular or rectangular cross-sections. Also, the filars may be electrically conductive so as to act as an electrical conductor between a contact pin of a lead connective end (e.g., an IS-1 connector) and a tip electrode of the lead. The coil can also act as a stiffener for the lead to enhance lead pushability and torquability. The coil can also reduce the likelihood of devices passing through the lumen piercing the lumen 50.

The reinforcing structure 55 may extend about an outer circumferential surface 65 of the core wall 25. As described further below, the outer jacket 60 may encapsulate the reinforcing structure 55. As indicated in FIGS. 1A-B, the outer jacket 60 bonds to the outer circumferential surface 65 of the core wall 25. An outer circumferential surface 75 of the jacket 60 may form the outer circumferential surface of the implantable lead 10.

As indicated in FIG. 1A, the central lumen 50 and the one or more core wall lumens 30 may extend from the distal end 35 to the proximal end 40. As illustrated in FIG. 1B, the core wall lumens 30 extending through the core wall 25 may be used for various purposes. For example, in one embodiment, a conductor wire 85 may extend through a core wall lumen 30 from the proximal end 40 to one or more electrical devices (e.g., electrodes, tracking coils or sensors) located at the distal end 35. The conductor wire 85 may transmit an electrical current that is used to track the location of the implantable lead 10 or to diagnose and/or treat a medical condition. In one embodiment, the conductor wire 85 may be between approximately 0.001" and approximately 0.011" in diameter and is a conductor that may be a micro coil, coaxial cable, or single or multi-strand wire.

A core wall lumen 30 may also serve as a conduit for transporting a fluid between the distal and proximal ends 35, 40 of the implantable lead 10, for example, to treat of a medical condition, to inflate or deflate an occlusion balloon near the distal end 35, or to provide a radiopaque marker material for visualization.

FIG. 2A is a longitudinal sectional view of another embodiment of an implantable lead 10'. FIG. 2B is a cross-sectional view of the implantable lead 10' of FIG. 2A, taken along section line B-B in FIG. 2A.

The implantable lead 10' is similar to the implantable lead 10, but does not include the reinforcing structure 55. The implantable lead 10' may include distal and proximal ends 35', 40', a core 20' with a core wall 25' with an outer diameter $D_O$, core wall lumens 30', a central lumen 50' and an outer jacket 60'. The core wall 25' may include inner and outer circumferential surfaces 70' and 65', and the jacket 60' may include an outer circumferential surface 75'. As discussed above, the implantable lead 10' may include various lead components, such as a conductor wire 85'. As discussed further below, both of the implantable leads 10, 10' may include various other lead components, as appropriate or desired.

Figure 11:
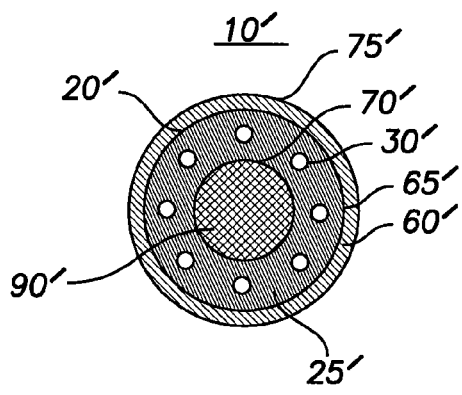
Figure 12:
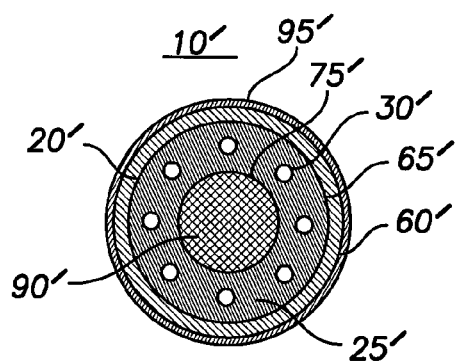
Figure 13:
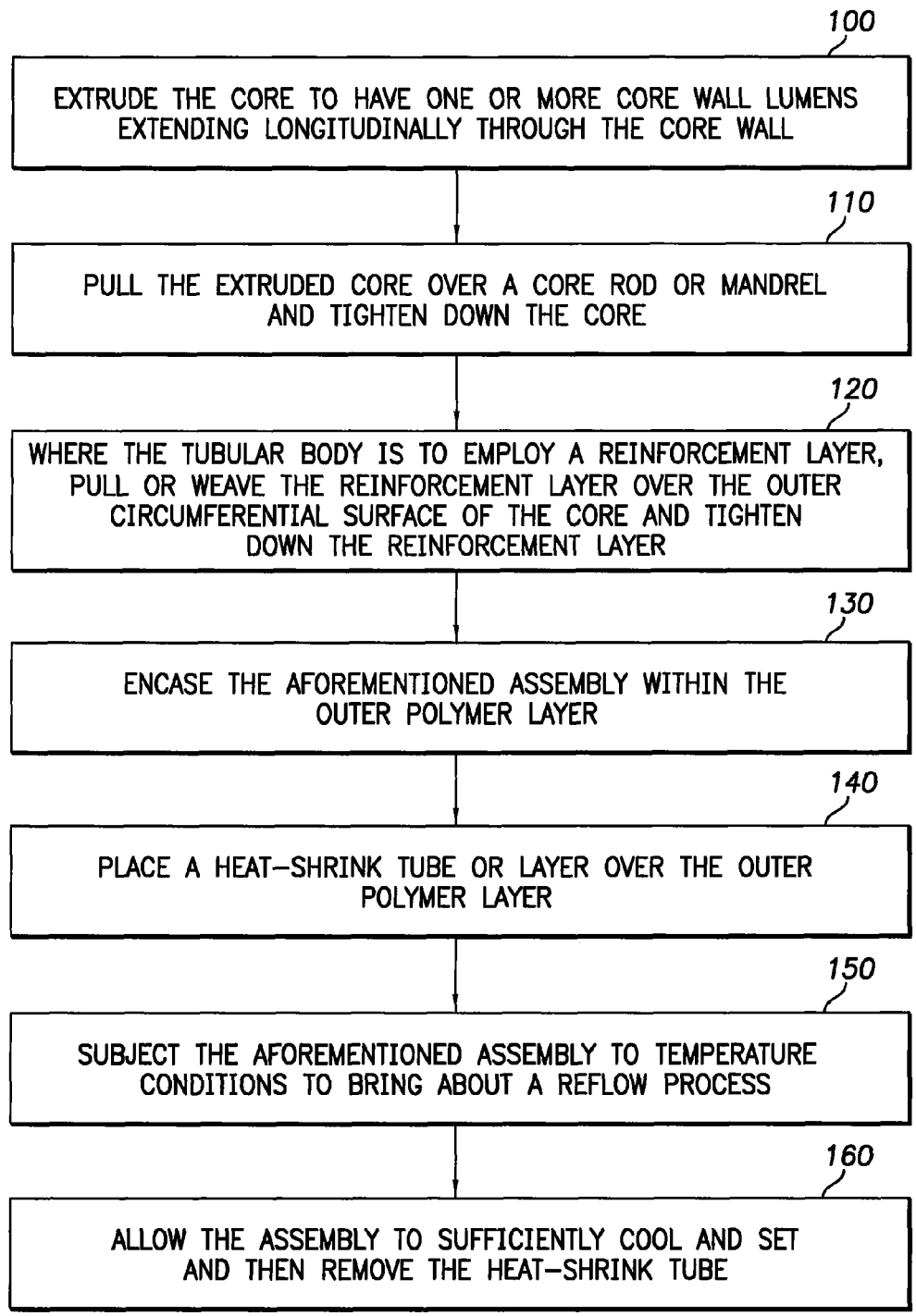
FIG. 13 is a flow chart outlining an exemplary method of manufacturing an implantable lead.

For a discussion of a method of manufacturing the implantable lead 10, reference is made to FIGS. 3-13. FIGS. 3-8 are cross-sectional views of the implantable lead 10 of FIGS. 1A-B at various stages of manufacture. FIGS. 9-12 are cross-sectional views of the implantable lead 10' of FIGS. 2A-B at various stages of manufacture. FIG. 13 is a flow chart outlining a method of manufacturing the implantable leads 10, 10'.

Figure 9:
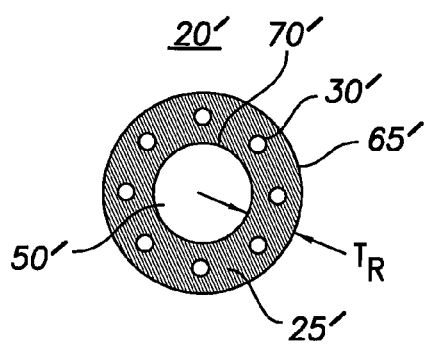
FIGS. 9-12 illustrate various stages of manufacture for the implantable lead of FIGS. 2A-B, in cross-section.

As depicted in FIGS. 3 and 9, in one embodiment, the core 20, 20' is extruded from a thermoset material, which is thermally stable during the reflow process (FIG. 13, block 100). In one embodiment, the thermoset material comprises PTFE, ePTFE, or silicone rubber. As the core 20, 20' is extruded, a circumferentially continuous core wall 25, 25' may be formed. The inner circumferential surface 70, 70' of the core wall 25, 25' may define the central lumen 50, 50'.

As illustrated, in one embodiment, the radial thickness $T_R$ of the core wall 25, 25' may be generally constant about the circumference of the core wall. However, it should be understood that the inner circumferential surface 70, 70' of the core wall 25, 25' may be non-circular and that the radial thickness $T_R$ of the core wall may vary about the circumference of the core wall.

Regardless of whether the radial thickness $T_R$ of the core wall 25, 25' is constant or not, the radial thickness $T_R$, in at least one location, may be sufficient to receive one or more core wall lumens 30, 30' longitudinally extending through the radial thickness $T_R$ of the core wall between the outer and inner circumferential surfaces 65, 65', 70, 70'. As depicted in FIGS. 3 and 9, in one embodiment, the core wall lumens 30, 30' may be evenly radially distributed or arrayed about the ring formed by a lateral cross-section of the core wall 25, 25'. However, it should be understood that the core wall lumens 30, 30' may be unevenly distributed about the circumference of the core wall 25, 25', and may be located at different radiuses from the longitudinal axis of the implantable lead 10, 10'. Regardless of the distribution pattern of the core wall lumens 30, 30', the core wall lumens may be integrally formed in the core wall 25, 25' during the extrusion process.

In one embodiment, the core 20, 20' is extruded from PTFE, which offers excellent thermal qualities and mechanical stability. Because of the radial thickness $T_R$ of the core walls 25, 25' and the qualities of PTFE, the core wall lumens 30, 30' may not collapse when the core 20, 20' is extruded or subjected to the reflow process, discussed below.

Figure 4:
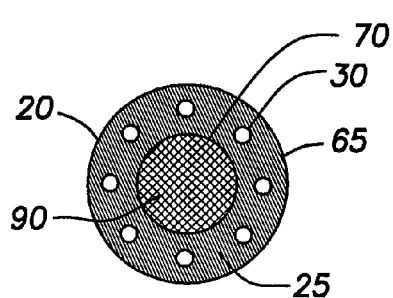
Figure 10:
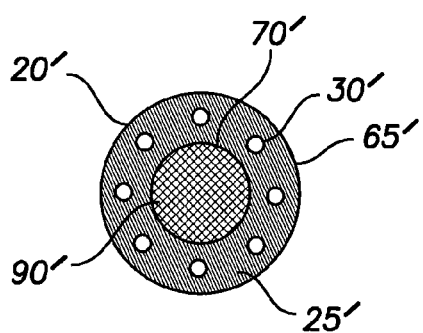

As indicated in FIGS. 4 and 10, the extruded core 20, 20' may be pulled over a core rod or mandrel 90, 90' and tightened down or otherwise secured (FIG. 13, block 110). The mandrel 90, 90' may support the core 20, 20' during manufacture of the lead 10, 10'. More specifically, the mandrel may act to keep the core straight during the reflow process. It should be understood that the mandrel 90, 90' may be situated within the core 20, 20' in any suitable manner, for example, by pushing the mandrel into the core or extruding the core over the mandrel.

Figure 5:
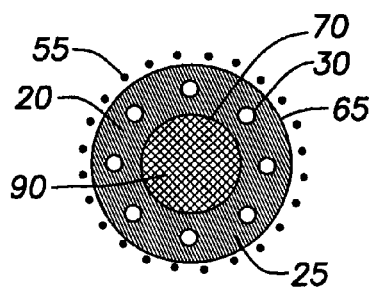

As illustrated in FIG. 5, a reinforcing structure 55, such as a cylindrical or flat wire braid, may be pulled or woven over the outer circumferential surface 65 of the core 20 and tightened down or otherwise secured (FIG. 13, block 120). Although the reinforcing structure 55 may be a braid, as shown, it should be understood that any suitable configuration may be used, such as one or more coils, parallel wires or a mesh. Further, it should be understood that any suitable material that is capable of providing reinforcement to the materials of the core 20, 20' and/or the jacket 60, 60' may be used, including but not limited to metals (e.g., stainless steel 316LVM, MP35NLT, and the like) and polymers (polyester, nylon, VECTRAN™, and the like).

Figure 6:
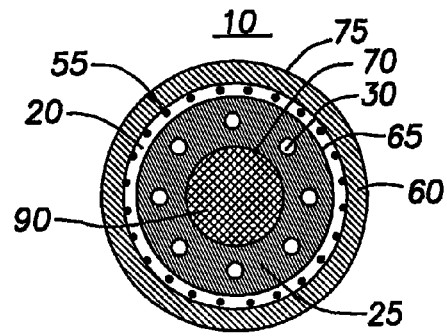

As shown in FIGS. 6 and 11, the entirety of the aforementioned components may then be surrounded by the outer jacket 60, 60' (FIG. 13, block 130). For example, in one embodiment, the outer jacket 60, 60' comprises an extruded polymer material that is pulled over or otherwise positioned around the aforementioned components and tightened down or otherwise secured. In another embodiment, the outer jacket 60, 60' is extruded over the aforementioned components or, alternatively, extruded and then pulled over the aforementioned components. In one embodiment, the outer jacket 60, 60' comprises a polymer material such as polyurethane (e.g., pellathane 55D), OPTIM®, PIBS, CARBOSIL™, etc. In one embodiment, the outer jacket 60, 60' comprises a polymer material having a durometer value of between approximately 25 Shore A hardness to approximately 55 Shore D hardness. The material of the outer jacket 60, 60' may be selected based on flex-fatigue endurance, abrasion resistance, stiffness, resistance to corrosion, column strength, metal ion oxidation (MIO), environmental stress cracking (ESC), etc.

Figure 7:
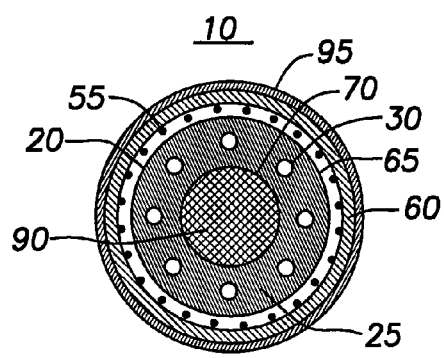

As depicted in FIGS. 7 and 12, a heat-shrink tube or layer 95, 95' may be placed over the outer jacket 60, 60' (FIG. 13, block 140). In one embodiment, the heat-shrink tube 95 comprises a polymeric material, such as FEP (fluorinated ethylene propylene). In one embodiment, the heat-shrink tube 95 may include a shrink temperature ranging from approximately 350 degrees Fahrenheit to approximately 450 degrees Fahrenheit. IN any case, it should be understood that the heat-shrink tube 95 should have a shrink temperature that is compatible with a reflow temperature of the material of the jacket 60, 60', as discussed below. Similarly, the material of the core 20, 20' should have a melt temperature that is higher than the reflow temperature of the material of the jacket 60, 60', to avoid melting or softening the core to a point of deformation, which may undesirably alter a desired shape of the core, close lumens and/or allow components to shift position.

The assemblies depicted in FIGS. 7 and 12 may be subjected to heating to a sufficient temperature to achieve shrinking of the heat-shrink tube 95, 95' and reflow of the material of the jacket 60, 60', such as to the aforementioned temperature conditions (FIG. 13, block 150). The jacket 60, 60' in turn will melt, encase or encapsulate the reinforcing structure 55 (where present), and consolidate with the outer circumferential surface 65, 65' of the core 20, 20'.

By consolidating, the material of the jacket 60, 60' bonds to the core 20, 20', either by chemical interaction, molecular interaction, simple compression or physical engagement. In particular, any known or hereafter developed primer or surface treatment may be used to enhance the bonding. For example, the core 20, 20' may be formed of PTFE and chemically etched on the outer circumferential surface 65, 65'.

In one embodiment, the materials of the core 20, 20' and the outer jacket 60, 60' are chemically compatible such that they can be thermally bonded at the interfaces between the materials. In another embodiment, where the various polymeric materials are not necessarily chemically compatible such that they will thermally bond, the interfacing surfaces of the various materials may be subjected to physical or chemical surface modification to achieve reliable surface bonding. Physical surface modification may include plasma, corona, and laser surface treatments. Chemical surface modification may include chemical etching methods. However, it should be understood that outright chemical compatibility between the various materials or surface modification may not be necessary for reliable bonding into an integral structure.

When heat is applied, shrinking of the heat-shrink tube 95, 95' may generate pressure on the outer jacket 60, 60'. Further, the heat-shrink tube 95, 95' may transfer thermal energy to liquefy the outer jacket 60, 60'.

To ensure that the outer jacket 60, 60' is completely liquefied during the reflow process, the shrink temperature of the heat-shrink tube 95, 95' may be higher than the softening or melting temperature of the outer jacket 60, 60'. The combination of heat and pressure during the reflow process may result in an integral implantable lead 10, 10', for example, via melt flow of the material of the jacket 60, 60' and bonding to the core 20, 20' and possibly the other lead components.

Figure 8:
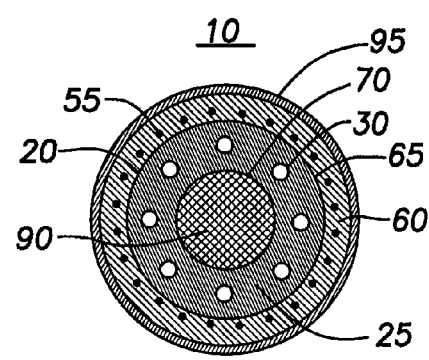

Once the reflow process is complete, the assembly appears as depicted in FIG. 8 or 12. Once the implantable lead 10, 10' is sufficiently cooled and set, the heat-shrink tube 95 may be removed from the implantable lead 10, 10' (FIG. 13, block 160). The implantable lead 10, 10' then appears as shown in FIG. 1B or 2B.

Once the reflow process, including cooling, is completed, various lead components (e.g., conductor wires 85, 85', etc.) may be inserted into their respective core wall lumens 30, 30'. Alternatively, various lead components may be included prior to the reflow process, such as with the reinforcing structure 55. When included, the lead components may be encased and/or bonded by the flow of the material of the jacket 60, 60'. However, where appropriate or desired, such lead components may be prevented from such bonding, for example, by including a compliant material, as described below.

Figure 14A:
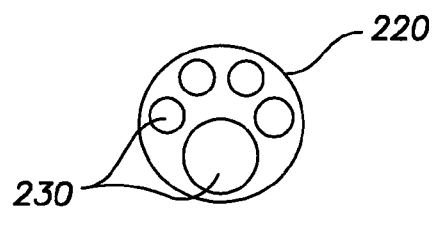
FIGS. 14A-B are cross-sectional views of embodiments of a core for an implantable lead.
Figure 14B:
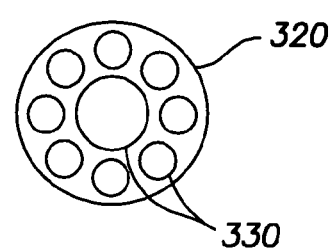

FIG. 14A is a cross-sectional view of a core 220 including a plurality of lumens 230. FIG. 14B is a cross-sectional view of a core 320 including a plurality of lumens 330. FIGS. 14A-B illustrate different lumen configurations that may exist in leads constructed via the above-described reflow process. It should be understood that there may be a greater or lesser number of lumens, and that the lumens may be positioned as desired for a given application. As discussed further below, other lumen configurations are also contemplated.

Figure 15:
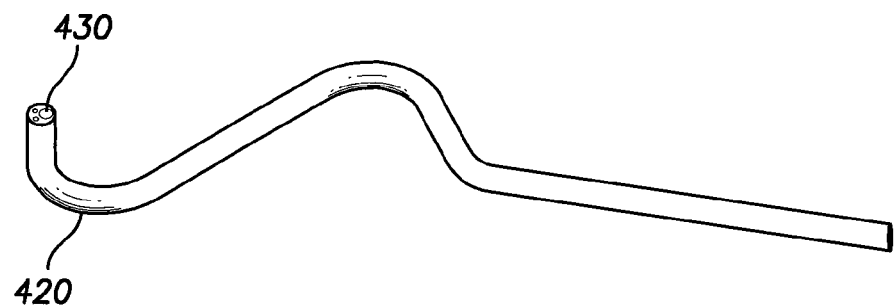
FIG. 15 is a perspective view of an embodiment of another embodiment of a core for an implantable lead.

FIG. 15 is a perspective view of a core 420 that includes a shape suitable for passive fixation of an implantable lead. The core 420 may be pre-shaped and may comprise silicone rubber, for example. The core 420 may include a number of lumens 430, for example, for shaping wires, conductors, delivery tools, etc. Such shaped passive fixation leads can be manufactured via the above-described reflow process.

As noted above, the various cores may comprise PTFE for applications in which the relative stiffer characteristics of PTFE are desirable. For example, column strength (pushability) provided by PTFE may aid in functionality, implantability, and/or handling of the implantable lead. PTFE may also be extruded under relatively tighter tolerance standards than other materials, such as silicone rubbers or urethanes. This may facilitate smaller lumens, thinner inter-luminal walls, and the like, which may facilitate downsizing of the implantable lead without undesirably compromising features, such as the number of conduction paths. PTFE also provides innate lubricity, which may also facilitate downsizing and reducing clearances between components. Also, PTFE reduces friction between the lead and intra-lumen delivery tools (e.g., stylets, guidewires, etc.).

Silicone rubber may be used for the core material for applications in which the relative softer characteristics of silicone rubber are desirable. The various implantable leads should be flexible and compliant. For example, stiffness in a RV (right ventricle) lead may result in undesirable perforation of tissue. Also, as discussed above, silicone rubber may be used for the core material when a set flexible shape is important, for example, S-shapes or J-shapes for passive fixation, or longitudinal curves configured to absorb compressive forces.

Figure 16A:
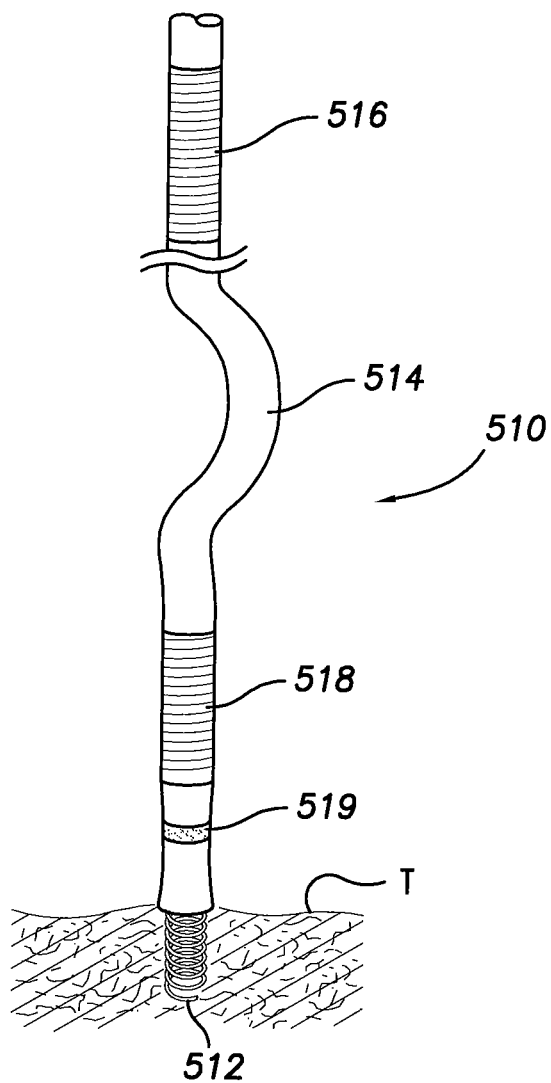
FIG. 16A is a longitudinal view of an embodiment of an implantable lead including a shock-absorbing feature.
Figure 16B:
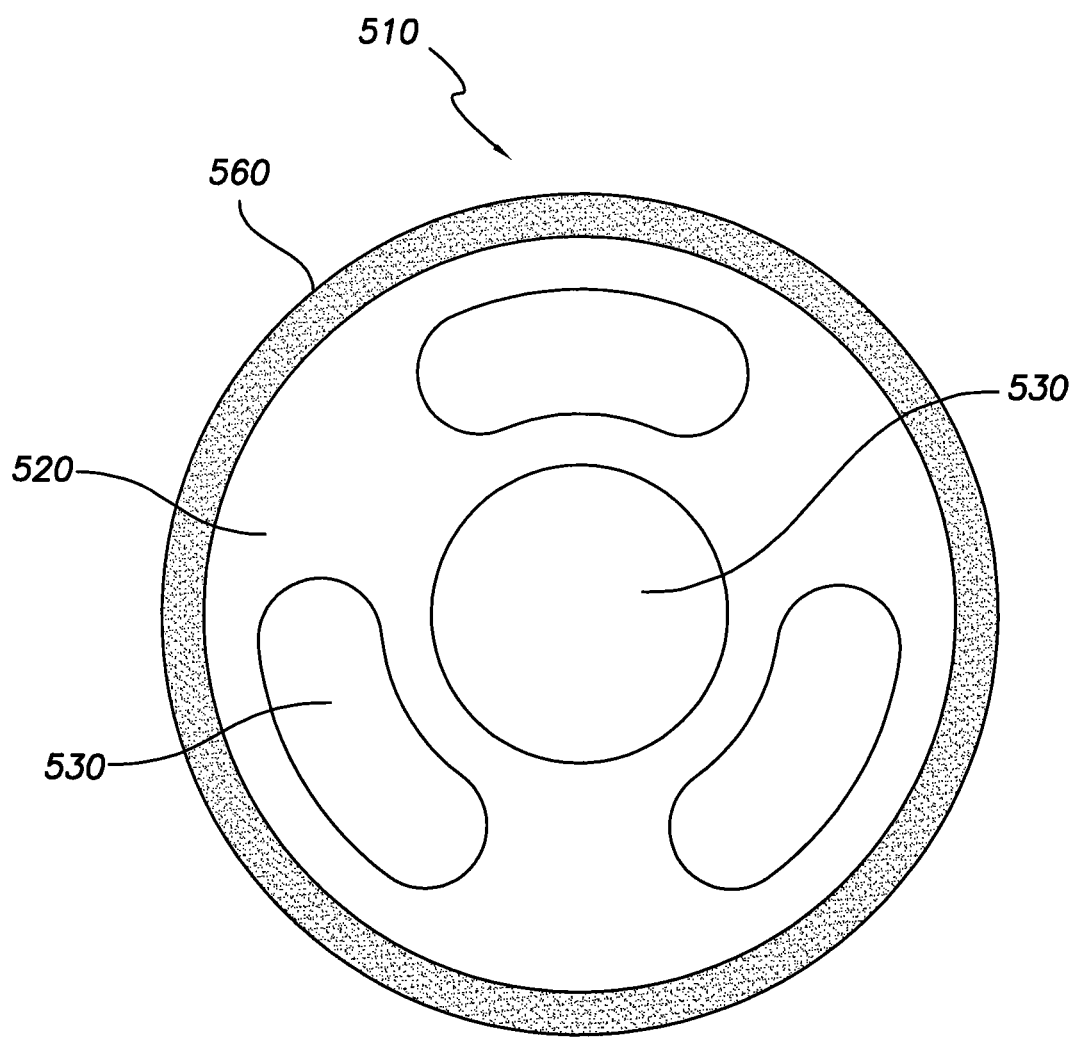
FIG. 16B is a cross-sectional view of the implantable lead of FIG. 16A.

FIG. 16A is a longitudinal view of an embodiment of an implantable lead 510 including a shock-absorbing feature. FIG. 16B is a cross-sectional view of the implantable lead 510. The implantable lead 510 may include a core 520 including a plurality of lumens 530 and a jacket 560, similar to the embodiments discussed above. Further, the implantable lead 510 may include a distal helix 512 that may be affixed to tissue T, for example, by screwing. The shock-absorbing feature may be provided by a shape 514 set into the core 520. Reflow of the jacket 560 as described above would be after the shape is set in the core 520.

The shape 514 may be a longitudinal curve that is adapted to absorb stresses, for example, caused by longitudinal movement of the lead 510, that would otherwise be transmitted to the distal helix 512, which may dislodge the distal helix 512 and/or damage (e.g., perforate) the tissue T. The flexibility and resiliency of the core 520 may allow the shape 514 to alter (e.g., buckle) and absorb a longitudinal stress (compressive force) applied to the implantable lead 510.

As shown, the implantable lead 510 may also include one or more shock coils 516, 518. For example, the lead 510 may have a SVC shock coil 516 and a RV shock coil 518. The lead may also include one or more electrodes 519 for pacing and/or sensing. As described later in this Detailed Description, in some embodiments, the above-described reflow process can be used to reflow polymer material into the gaps between the filars or coils of the shock coil, resulting in a shock coil that is less likely to be susceptible to tissue ingrowth.

FIG. 17 is a longitudinal view of an implantable lead 610 including a composite core, i.e., a combination of different core materials. Such a lead can be manufactured via the above-described reflow process. Using different core materials along the length of an implantable lead may alter the mechanical characteristics of different sections of the lead. For example, a LV (left ventricle) lead may require good column strength along most of the lead to allow the lead to be pushed along a guide wire into coronary veins, while requiring the distal end to be flexible to track acute bends in tortuous anatomy.

As illustrated in FIG. 17, a distal section 612 may include a shape-set silicone rubber core, as discussed above, for passive fixation. The distal section 612 may also provide desired flexibility and trackability of the lead 610. A proximal section 614, such as adjacent the distal section 612, may include a PTFE core, which may provide desired column strength for pushability and/or torque, etc. Further, although not shown, multiple transitions between silicone and PTFE core may be provided along the length of the lead to provide shock absorption and help avoid perforation, as discussed above.

Figure 18B:
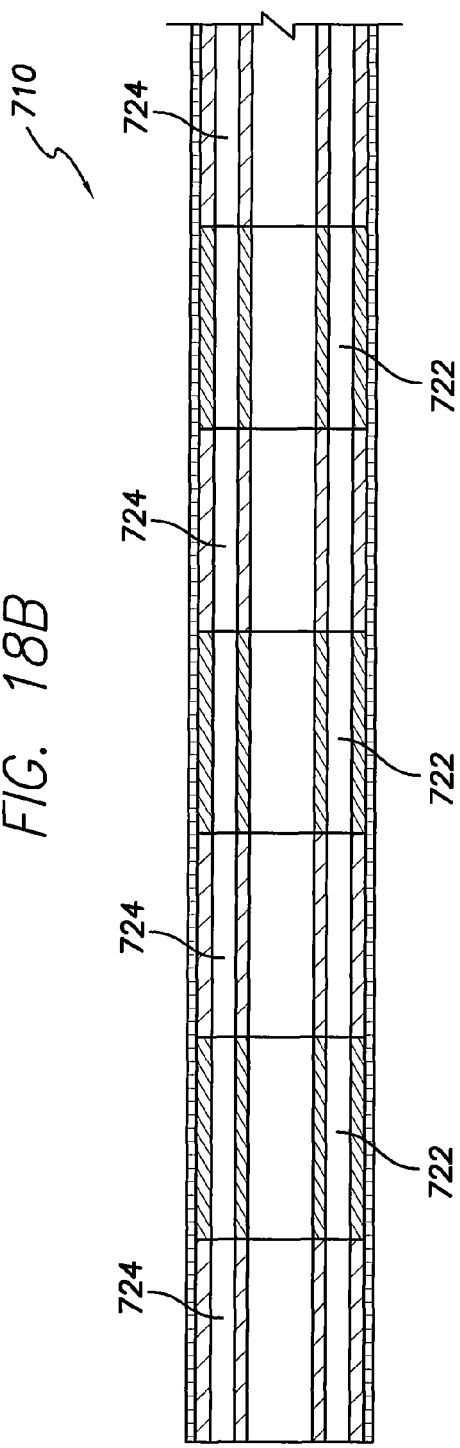
FIG. 18B is the same view as FIG. 18A, except as viewed from the side.

FIGS. 18A and 18B are, respectively, isometric and side views of a partial longitudinal section of an implantable lead 710 including a sectioned composite core. Such a lead can be manufactured via the above-described reflow process. In this embodiment, different core materials are spaced apart along the length of the lead 710. Varying the lengths of transitions, number of transitions and locations of transitions may allow mechanical characteristics to be altered and/or optimized along the length of the lead 710.

For example, an RV (right ventricle) lead may require compressive force/shock absorption along the lead to help reduce risk of tissue perforations by the tip of the lead. As illustrated in FIG. 18, PTFE core segments 722 and silicone core segments 724 may be longitudinally interspersed. The arrangement may provide durometer transitions that help facilitate buckling to help prevent compressive forces from being transmitted to the distal tip or attachment point of the lead 710, which may otherwise damage the tissue.

Figure 19A:
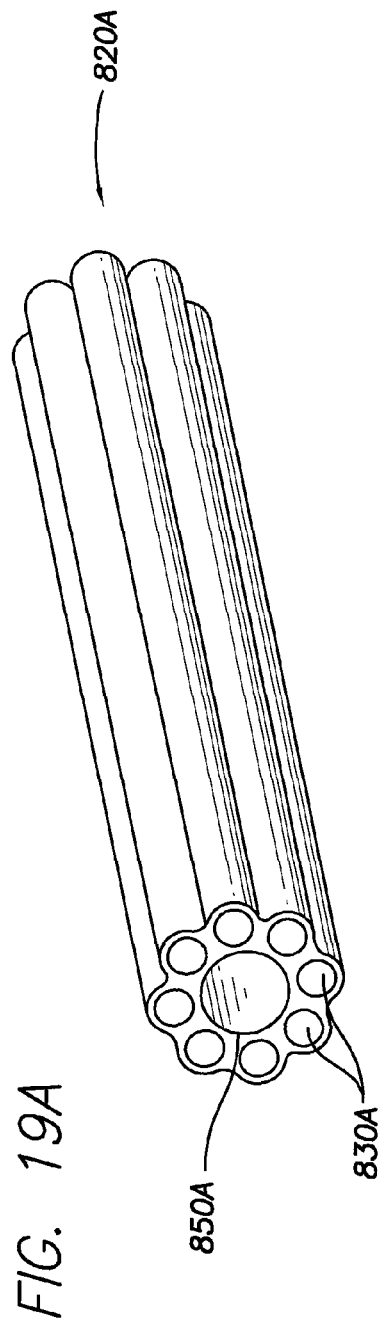
FIGS. 19A-B are perspective views of embodiments of non-circular cores for an implantable lead.
Figure 19B:
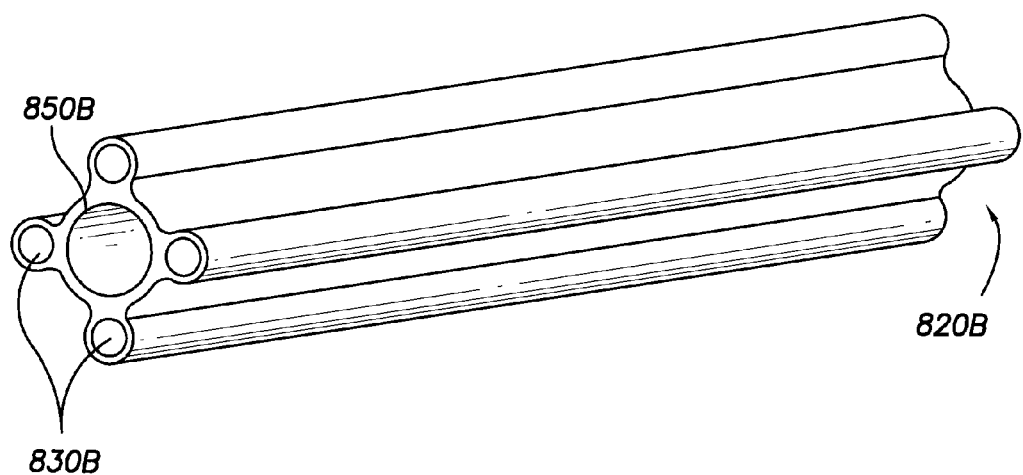

FIGS. 19A-B are perspective views of non-circular cores for an implantable lead. Such non-circular cores may provide more flexibility, for example, in cases that PTFE material cannot be replaced by silicone rubber material. Such non-circular cores can be employed to manufacture leads using the above-described reflow process.

In FIG. 19A, a non-circular core 820A including a plurality of peripheral lumens 830A and a central lumen 850A may have material removed from an extruded core body. In particular, material from between the peripheral lumens 830A may be removed to present a non-circular outer surface. Alternatively, the core 820A may be extruded to have the non-circular outer surface. The spaces between the peripheral lumens 830A may provide increased flexibility to the core 820A by reducing the bending moment of inertia of the core 820A.

In FIG. 19B, a non-circular core 820B having a different configuration of peripheral lumens 830B and a central lumen 850B may also have material removed from an extruded core body. In particular, material from between the peripheral lumens 830B may be removed to present a non-circular outer surface. Alternatively, the core 820B may be extruded to have the non-circular outer surface. The spaces between the peripheral lumens 830B are comparatively larger, which may provide relatively more flexibility to the core 820B.

Figure 20A:
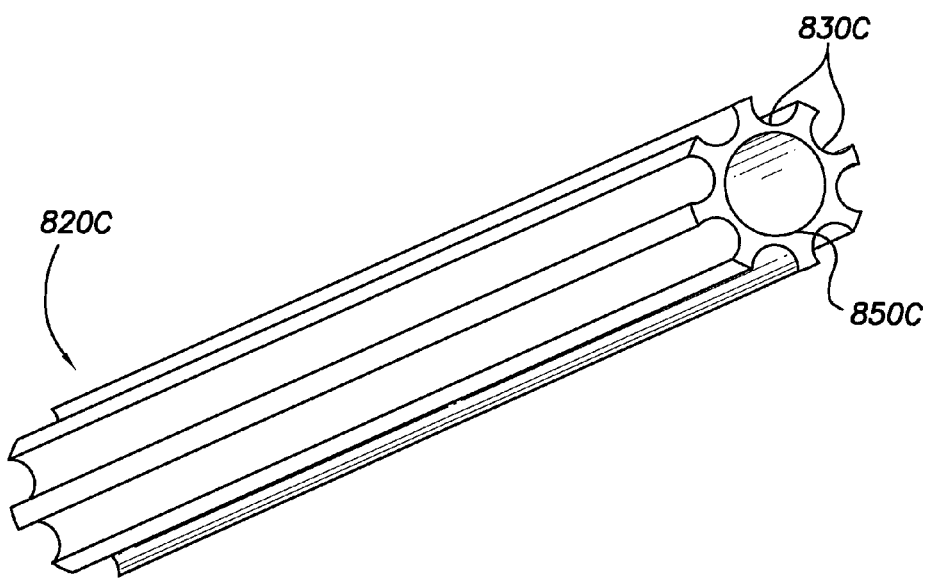
FIGS. 20A-B are perspective views of embodiments of non-circular cores including open lumens.
Figure 20B:
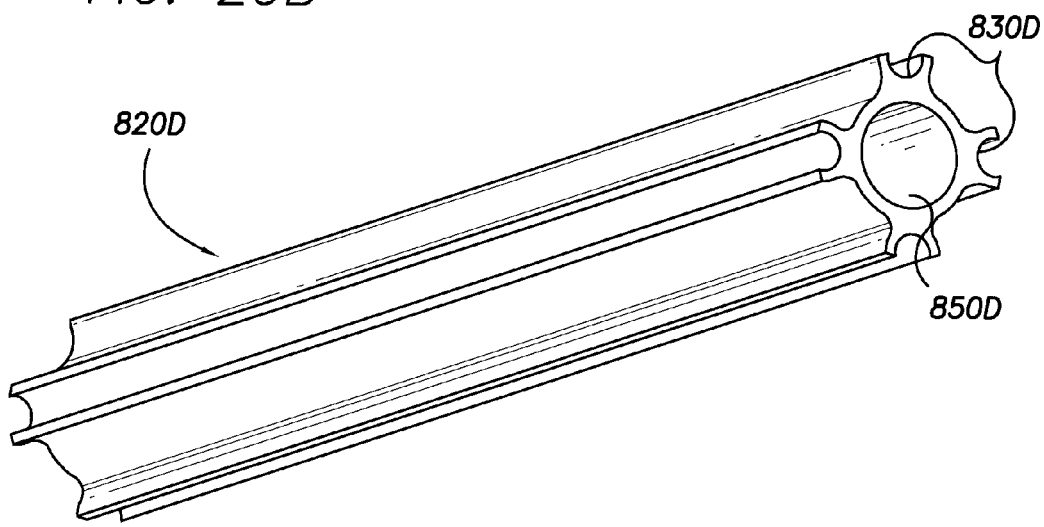

FIGS. 20A-B are perspective views of other non-circular cores including open lumens. Such non-circular cores may further increase flexibility by further reducing the bending moment of inertia of the cores. Such non-circular cores can be employed to manufacture leads using the above-described reflow process.

In FIG. 20A, a non-circular core 820C including a plurality of peripheral lumens 830C and a central lumen 850C may have additional material removed as compared to the core 820A in FIG. 19A. In particular, material may be removed to open the peripheral lumens 830C radially outward. In addition to increased flexibility for the core 820C, the open lumens/channels/grooves 830C may facilitate placement of lead components (e.g., conductor wires, crimp-slugs, etc.) therein. The components placed in the open lumens 830C may also be secured by the material of the jacket during the reflow process. Alternatively, a compliant material, such as hydrogel, may fill in around the lead components in the open lumens/channels/grooves 830C to avoid bonding of the jacket material to the lead components.

FIG. 20B illustrates a similar further modification of the non-circular core 820B of FIG. 19B. A non-circular core 820D may include a plurality of open lumens 830D, formed by additional material being removed from the peripheral lumens 830B in FIG. 19B, and a central lumen 850D.

Figure 21A:
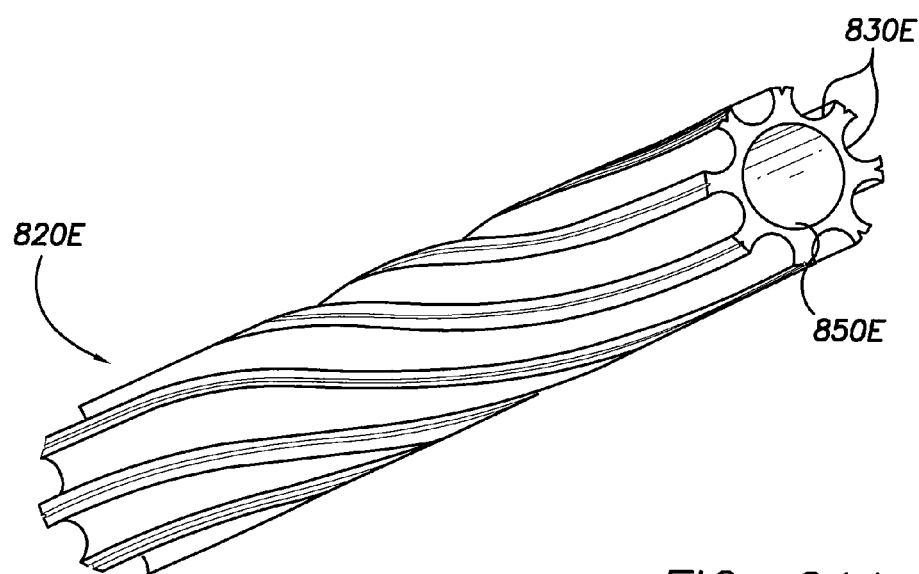
FIGS. 21A-B are perspective views of embodiments of non-circular cores including open lumens with a helical configuration.
Figure 21B:
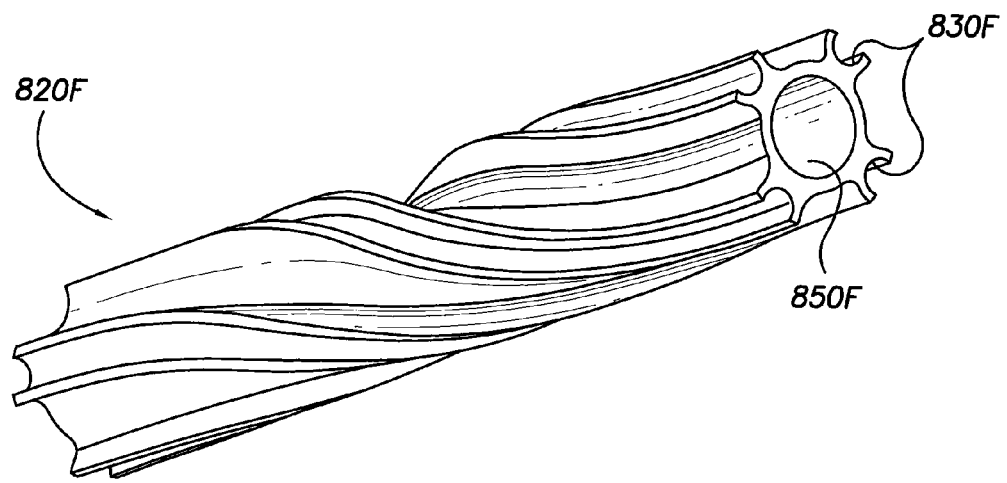

FIGS. 21A-B are perspective views of other non-circular cores including open lumens with a helical configuration. Such non-circular cores may add strain relief. Such non-circular cores can be employed to manufacture leads using the above-described reflow process.

In FIG. 21A, a non-circular core 820E including a plurality of open lumens 830E and a central lumen 850E similar to the core 820C in FIG. 20A. However, core 820E includes a helical or spiral twist around a central axis of the core 820E. Alternatively, for embodiments employing PTFE cores, since PTFE naturally twists during extrusion, the natural tendency to twist is leveraged for the benefit of obtaining the twisted core depicted in FIG. 21A.

FIG. 21B illustrates a similar further modification of the non-circular core 820F of FIG. 20B. A non-circular core 820F may include a plurality of open lumens 830F and a central lumen 850F similar to the core 820D in FIG. 20B. However, core 820F includes a helical or spiral twist around a central axis of the core 820F.

Non-circular cores, such as those illustrated in FIGS. 19A-21B, may provide space for lead components to rest or slide during assembly for manufacture of an implantable lead. Such an approach may reduce or even eliminate clearance issues between the core and mating components to be assembled to the core. As discussed herein and illustrated in FIGS. 22A-B, the reflow process may consolidate the assembly of the core and components, bonding the components in place or allowing a desired freedom of movement within the assembled lead.

Figure 22A:
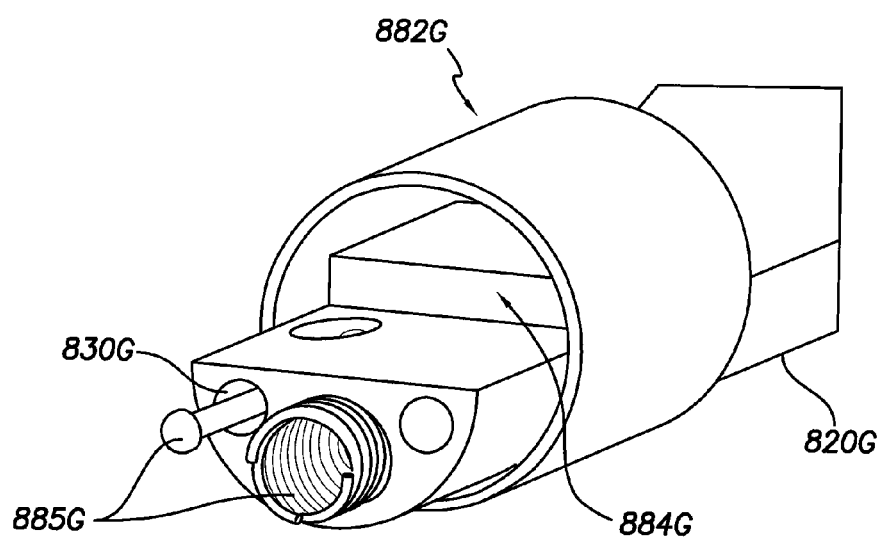
FIGS. 22A-B are partial perspective views of an embodiment of an implantable lead including a non-circular core and various lead components, before and after reflow of the jacket.
Figure 22B:
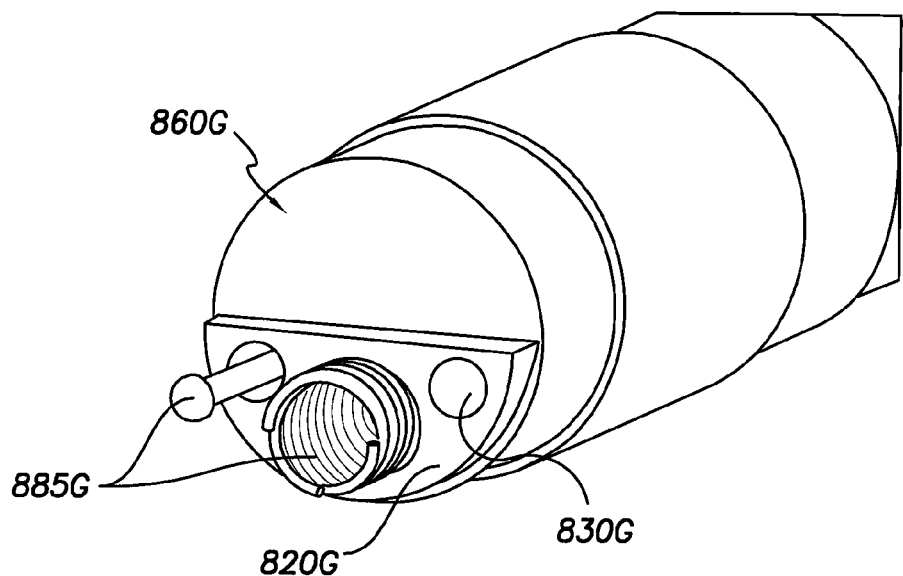

As illustrated in FIG. 22A, a non-circular core 820G may have conductors 885G, a ring electrode 882G, and various other lead components 884G (e.g., active or passive component, crimp-slug, etc.) assembled thereon, such as in a lumen 830G. As shown, the non-circular core 820G provides clearance for components that may otherwise be difficult to fit, for example, within the outer diameter of the lead. Such non-circular cores can be employed to manufacture leads using the above-described reflow process.

The ring electrode 882G may be situated on an outer surface of the core 820G such that the jacket 860G (shown in FIG. 22B) abuts the ring electrode 882G, but does not cover the ring electrode 882G. Thus, when heat is applied to cause the material of the jacket 860G to flow, the ring electrode 882G remains exposed because the FEP heat shrink tube 95 is self-masking over the electrode. However, the material of the jacket 860G flows during the reflow process to consolidate the assembly, flowing on both sides of the ring electrode 882G and fixing both the ring electrode 882G and the other components 884G in place.

Figure 23:
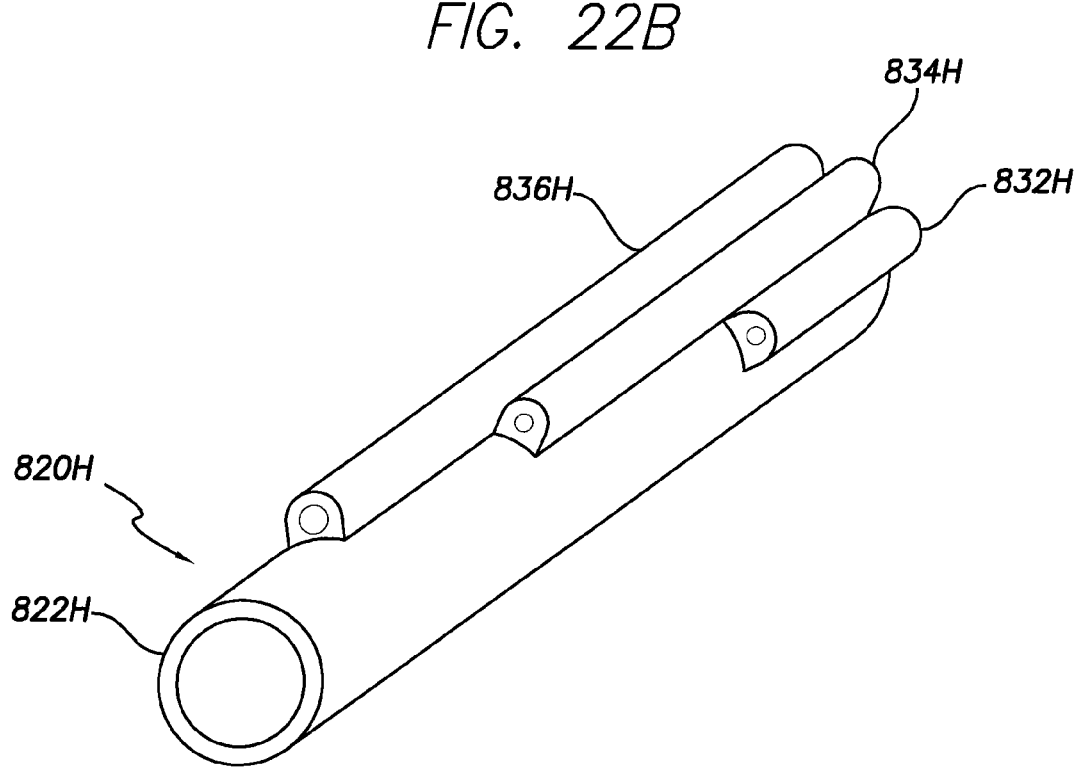
FIG. 23 is a partial perspective view of an embodiment of a non-circular core including a plurality of peripheral longitudinal lumens.

FIG. 23 is a partial perspective view of another non-circular core 820H including a plurality of peripheral longitudinal lumens, specifically, a first lumen 832H, a second lumen 834H and a third lumen 836H, although any desired number of lumens may be included. Such non-circular cores can be employed to manufacture leads using the above-described reflow process.

As shown, each of the lumens 832H, 834H and 836H terminates at a different longitudinal position. By progressively terminating the lumens, a progressive increase in the flexibility of the core 820H may be obtained. In particular, "dropping" a lumen before reaching a distal end 822H of the core 820H may result in a desirably more flexible distal end 822H for the implantable lead including the core 820H. Further, dropping a lumen may provide additional clearance for components to be assembled to the core. For example, a ring electrode (not shown) may be assembled adjacent a "dropped" lumen to allow a conductor disposed in that lumen to be connected thereto.

Figure 24:
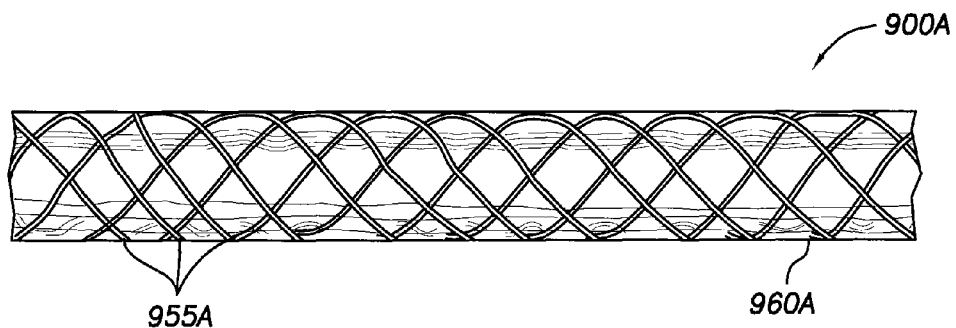
FIG. 24 is a longitudinal view of an embodiment of an implantable lead including a braid wire and a transparent jacket.

FIG. 24 is a longitudinal view of an implantable lead 900A including a braid wire 955A and a transparent jacket 960A. Such a lead can be manufactured using the above-described reflow process. The braid wire 955A may serve as a reinforcing structure, as discussed above. Alternatively or additionally, the braid wire 955A may serve as an electromagnetic shield. For example, such a shield may guard against exposure to electromagnetic interference, which may be especially beneficial for compatibility with traditional diagnostic and imaging techniques, such as nuclear magnetic resonance imaging ((N)MRI).

Figure 25:
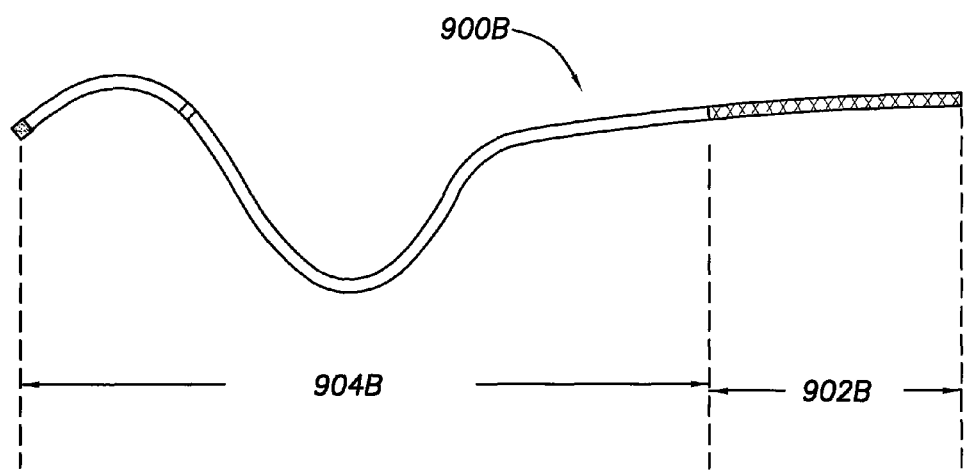
FIG. 25 is a longitudinal view of an embodiment of an implantable lead including a reinforcing structure over a first longitudinal section, but not over a second longitudinal section.
Figure 26:
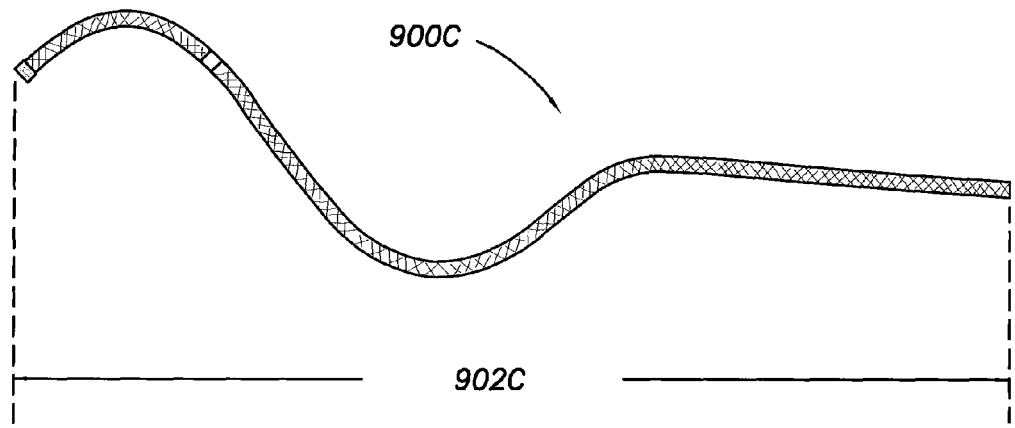
FIG. 26 is a longitudinal view of an embodiment of an implantable lead including a reinforcing structure over an entire length.

FIG. 25 is a longitudinal view of an implantable lead 900B including a reinforcing structure over a first longitudinal section 902B, but not over a second longitudinal section 904B. FIG. 26 is a longitudinal view of an implantable lead 900C including a reinforcing structure over an entire length 902C. Further, although not shown, small lengths of reinforcing structure may be positioned in strategic locations along the lead, for example, to enhance abrasion resistance and/or to otherwise protect lead components (e.g., electrode wires or coils) disposed in such locations. Such leads can be manufactured via the above-described reflow process.

Figure 27:
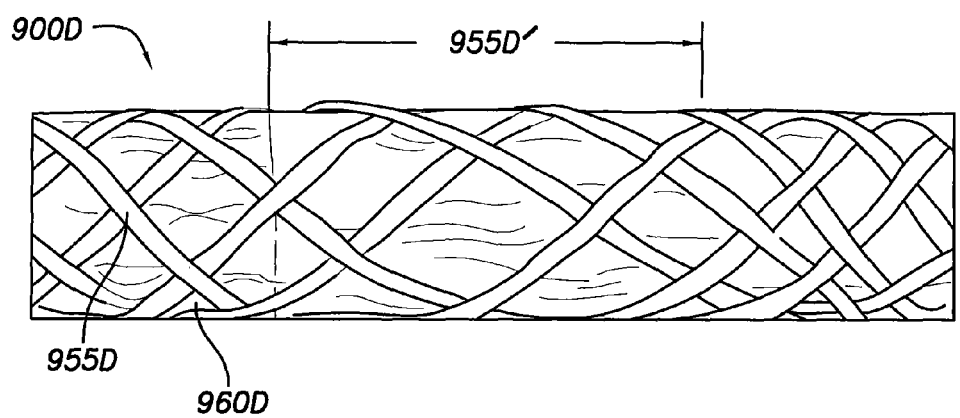
FIG. 27 is a partial longitudinal view of an embodiment of an implantable lead including a braid wire and a transparent jacket, with part of the braid wire exposed.

FIG. 27 is a partial longitudinal view of an embodiment of an implantable lead 900D including a braid wire 955D and a transparent jacket 960D, with a braid wire portion 955D' exposed. Such a configuration may allow the braid wire 955D to serve as an electrical conduction path with the exposed braid wire portion 955D' serving as an electrode. This may provide an electrode that is isodiametric with the overall lead, facilitating implantation and trackability, as well as providing a flexible electrode. For use as an electrode, platinum or platinum-iridium may be the material of choice. Such a lead can be manufactured via the above-described reflow process.

With or without the exposed braid wire portion 955D', the braid wire 955D or individual wires thereof may serve as electrical conductors, for example, to connect to one or more electrodes, collectively or separately, along the lead. The foregoing uses of the braid wire 955D may provide significant space savings and may achieve desirable downsizing of the lead.

The methods described herein are an improvement over conventional bonding techniques, such as using silicone-based medical adhesive. Various benefits and advantages are discussed above, without being exhaustive. For example, manufacturing time may be significantly reduced using the reflow methods discussed above.

Certain components on leads can be susceptible to tissue ingrowth (for example, shock coils), which could be detrimental to the performance (mechanical and/or electrical) of the lead. U.S. patent application Ser. No. 11/431,976, filed May 10, 2006 and entitled "Implantable Lead Assembly with Polymer Filled Electrode," which is hereby incorporated by reference into the present application, discloses a method of overmolding a shock coil with a polymer material (e.g., silicone rubber) to fill in the gaps between shock coil filars or coils. The overmolded shock coil then undergoes additional processing to remove the excess silicone rubber covering the shock coil, leaving behind only the silicone rubber between the adjacent shock coil filars.

Like the above-mentioned overmolding process, the reflow process disclosed herein may be used to produce a lead having a shock coil with the gaps between the shock coil filars or coils filled in to inhibit or prevent tissue ingrowth. However, the process disclosed herein does fill in the gaps between the coil filars with a reflowed polymer and results in an implantable lead in less than one-tenth of the time needed using conventional techniques. A non-limiting example of the reflow process is as follows:

i. provide a multi-lumen silicone rubber core;
    ii. insert mandrels into lumens to maintain lumen integrity during the reflow process;
    iii. coat outside of core with adhesion promoter (optional);
    iv. reflow a polymer (Optim™) jacket over core by employing a FEP heat shrink tube about the polymer jacket;
    v. cut skives/windows to expose lumens in desired locations;
    vi. remove mandrels from lumens;
    vii. crimp desired crimp-slugs onto conductor cables;

viii. string cables through skives/windows and into associated lumens, positioning crimp-slugs in skives/windows for welding;

ix. expand shock coil(s) and slide over assembly body with weld area of shock coil in contact with crimp-slug;

x. weld shock coil(s) to crimp-slug(s);

xi. provide heat-shrink tube(s) over shock coil(s) and apply heat to reflow jacket under/around shock coil(s); and xii. remove the FEP heat-shrink tube(s), obtaining a final isodiametric lead with jacket material filling spaces between the shock coil(s).

Figure 28:
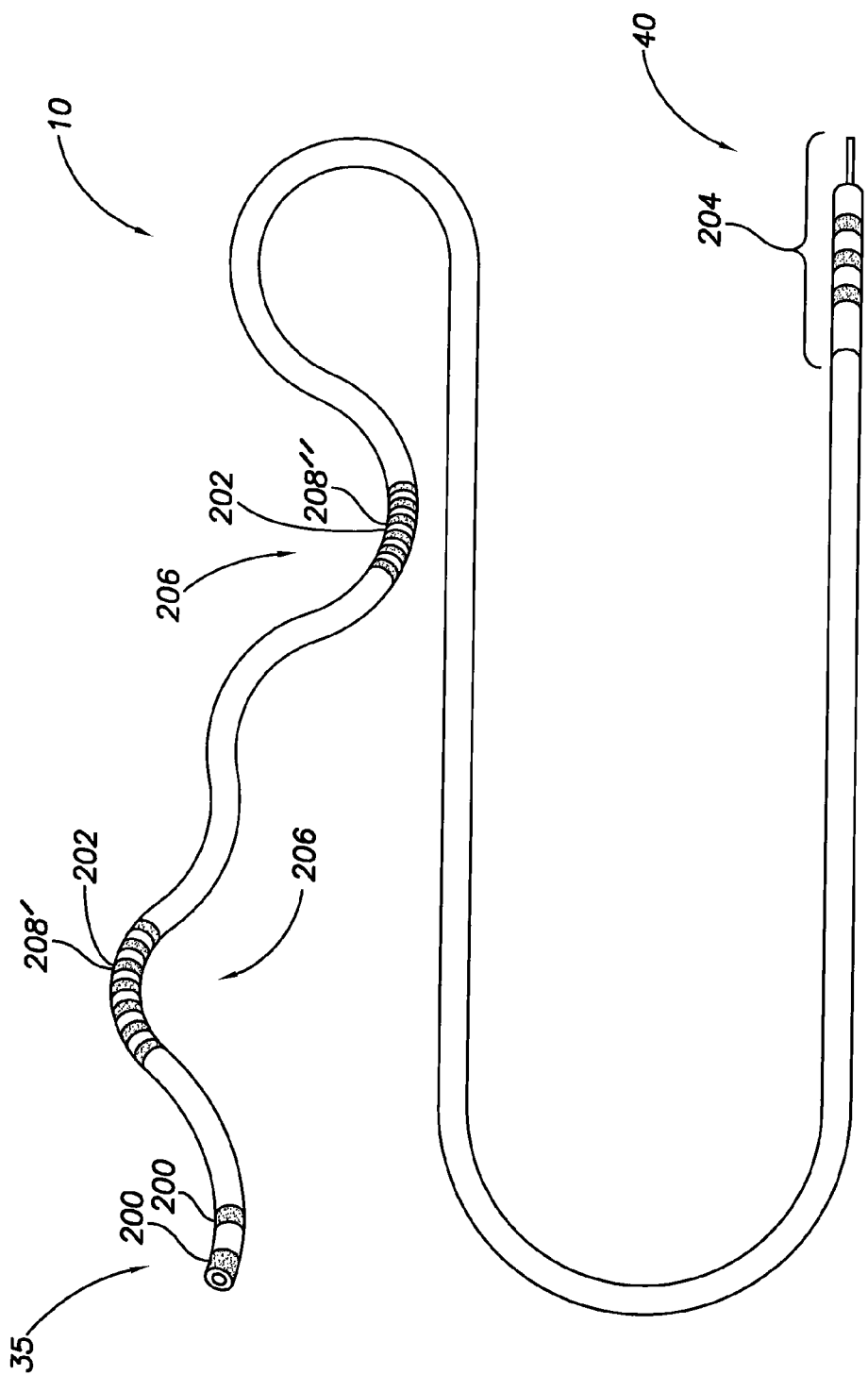
FIG. 28 is an isometric view of an implantable lead that has one or more pacing and/or sensing electrodes and/or one or more defibrillation electrodes or coils.

For a discussion of an implantable lead 10 that has one or more pacing and/or sensing electrodes 200 and/or one or more defibrillation electrodes or coils 202, reference is made to FIG. 28, which is an isometric view of such a lead 10. As shown in FIG. 28, the implantable lead 10 includes a distal end 35 for entering into a patient and a proximal end 40 for manipulation by a physician. The proximal end 40 terminates in a lead connector end 204 for coupling the proximal end 40 to an implantable pulse generator, such as a pacemaker, defibrillator or implantable cardioverter defibrillator. The lead 10 may include near the distal end 35 one or more pacing and/or sensing electrodes 200 and/or one or more defibrillation coils 202. In other embodiments, the lead 10 may include near the distal end 35 one or more pacing and/or sensing electrodes 200 and no defibrillation coils 202, or vice versa.

In one embodiment, the lead 10 is an implantable transvenous left ventricle ("LV") lead 10. The LV lead 10 may be designed for passive fixation and may have one or more pre-shaped curves 206 that bias into curved configurations when a stylet or guidewire used to deploy the lead is removed from the lead. In some such embodiments, the defibrillation coils 202 are located along the pre-shaped curves 206 and, in addition to facilitating defibrillation treatment, also assist in biasing the lead 10 into the pre-shaped curves 206. In other embodiments, the defibrillation coils 202 will be located away from the pre-shaped curves 206 or the defibrillation coils 202 will not be present at all, and the pre-shaped curves 206 are assisted in attaining the curved configuration by coils 208 that are completely imbedded in the outer jacket 60 of the lead 10.

For a general discussion of the components of the lead 10 discussed immediately above with respect to FIG. 28, reference is made to FIGS. 37 and 41. FIG. 37 is a transverse cross-section of the completed lead 10 in the area of a coil 208. FIG. 41 is an isometric view of a longitudinal section of the completed lead 10, wherein the outer jacket 60 is shown as a longitudinal cross-section to reveal the core 20 and coil 208. The coil 208 is depicted in FIGS. 37 and 41 as being completely imbedded in the jacket 60 and, in such an embodiment, would be for assisting in establishing a pre-shaped bend 206 in the lead 10. However, in other embodiments, as discussed below in greater detail and indicated in FIG. 28, the jacket 60 does not extend over an outer surface of the coil 208 such that the coil 208 is exposed to serve as a defibrillation coil 202. In such an embodiment, the defibrillation coil 202 may or may not also assist in establishing the pre-shaped bend 206 in the lead 10.

As shown in FIGS. 37 and 41, a polymer core 20 is provided and may include a central lumen 50, a circumferentially continuous core wall 25, and one or more core wall lumens 30 longitudinally extending within the radial thickness $T_R$ of the core wall 25. The core wall 25 may include an outer circumferential surface 65 and an inner circumferential surface 70 that defines the central lumen 50.

The core wall lumens 30 may provide space for various lead components, including functional components, (e.g., conductor wires and/or electrodes for transmitting an electrical current for medical condition diagnosis and/or treatment, stylets, guide-wires or other delivery tools, shaped wires, crimp-slugs, deflection wires for deflecting a portion of the lead for implantation or fixation purposes, etc.) to be positioned or introduced. The central lumen 50 may be open for the introduction of medical devices (e.g., stylets, guidewires, etc.) into the central lumen 50 by the physician.

As illustrated in FIGS. 37 and 41, the coil 208 may extend about the outer circumferential surface 65 of the core wall 25. As described further below, the outer jacket 60 may encapsulate the coil 208 as the outer jacket 60 bonds to the outer circumferential surface 65 of the core wall 25, and an outer circumferential surface 75 of the jacket 60 may form the outer circumferential surface of the implantable lead 10.

Alternatively and also as described further below, the outer jacket 60 may fill in the spaces between the individual filars of the coil 208 as the outer jacket 60 bonds to the outer circumferential surface 65 of the core wall 25. However, the outer surface of the coil 208 will be exposed to allow the coil 208 to act as a defibrillation coil 202. The coil outer surface and the outer circumferential surface 75 of the jacket 60 may therefore combine to form the outer circumferential surface of the implantable lead 10.

In a manner similar to the lead 10 depicted in FIG. 1A, the central lumen 50 and the one or more core wall lumens 30 of the lead 10 of FIGS. 28, 37 and 41 may extend from the distal end 35 to the proximal end 40. The core wall lumens 30 extending through the core wall 25 of the lead 10 of FIGS. 37 and 41 may be used for various purposes. For example, in one embodiment, a conductor wire 85 may extend through a core wall lumen 30 from the proximal end 40 to one or more electrical devices (e.g., pacing and sensing electrodes, defibrillation coils, etc.) located at the distal end 35. The conductor wire 85 may transmit an electrical current that is used to track the location of the implantable lead 10 or to diagnose and/or treat a medical condition. In one embodiment, the conductor wire 85 may be between approximately 0.001" and approximately 0.011" in diameter and is a conductor that may be a micro coil, coaxial cable, or single or multi-strand wire.

A window may be formed in the core wall 60 leading from a wall lumen 30 to the core outer circumferential surface 65. A conductor wire 85 will electrically connect to a pacing/sensing electrode 200 or a defibrillation electrode 202 by passing through the window from the lumen 30 to connect to an electrode 200 or coil 202.

A core wall lumen 30 may also serve as a conduit for transporting a fluid between the distal and proximal ends 35, 40 of the implantable lead 10, for example, to treat of a medical condition, to inflate or deflate an occlusion balloon near the distal end 35, or to provide a radiopaque marker material for visualization.

The core 20 of the lead 10 discussed with respect to FIGS. 28, 37 and 41 does not have to be configured like the cores 20 depicted in those figures. Instead, depending on the embodiment, the core 20 for the lead discussed with respect to FIGS. 28, 37 and 41 may have a variety of configurations, including any of the configurations depicted in FIGS. 14A, 14B, 16B, 18A, 18B, 19A, 19B, 20A, 20B, 21A, 21B and 23.

In one embodiment, the core 20 includes a polymer material, such as a thermoset material. In particular, PTFE (polytetrafluoroethylene), ePTFE (expanded-polytetrafluoroethylene), silicone rubber, or a combination of such materials, may be used for the core 20. The jacket 60 may include an extruded material, such as a thermoplastic material. In particular, materials such as polyurethane, Optim™ (ElastEon 2A), ElastEon 5, Carbosil™ (silicone polycarbonate urethane), Pebax® (polyether block amides), PIBS (polystyrene-b-polyisobutylene-b-polystyrene), etc. may be used for the jacket 60. In general, any suitable desired materials may be used for the core 20 and the jacket 60, as long as the jacket is reflowable at a temperature at which the core 20 is unaffected.

Figure 46:
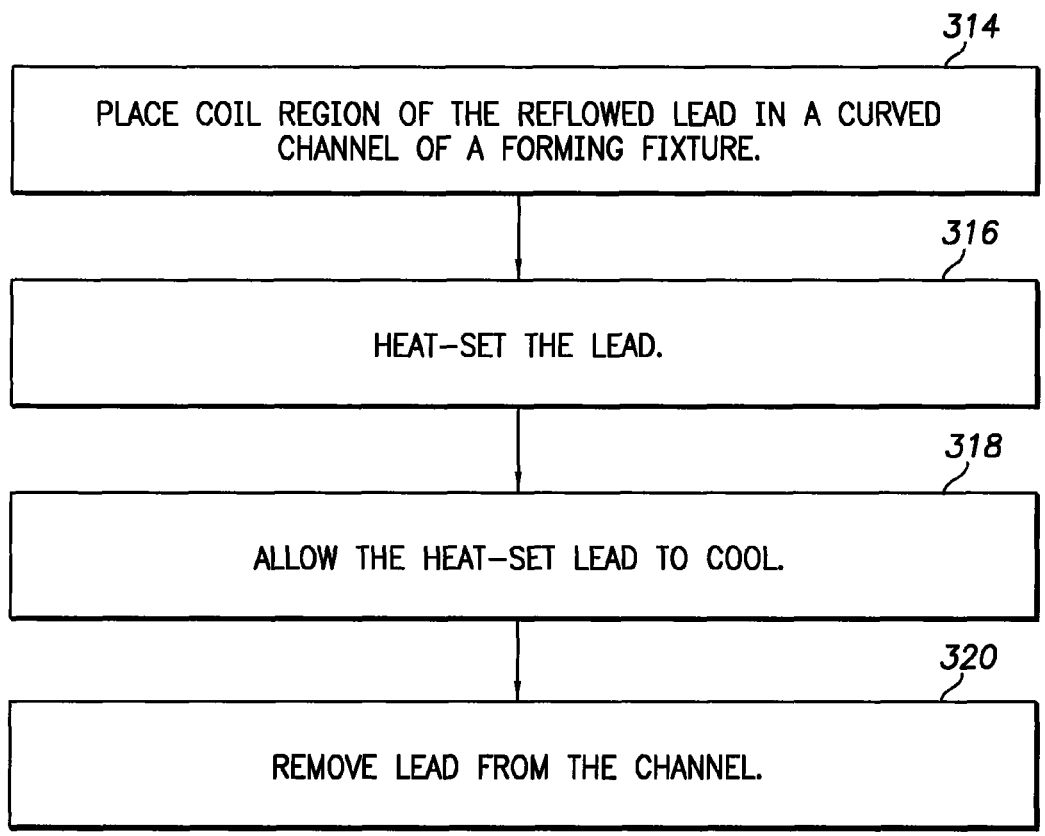
FIG. 46 is a diagram outlining the lead assembly processes illustrated in FIGS. 39-41.
Figure 47:
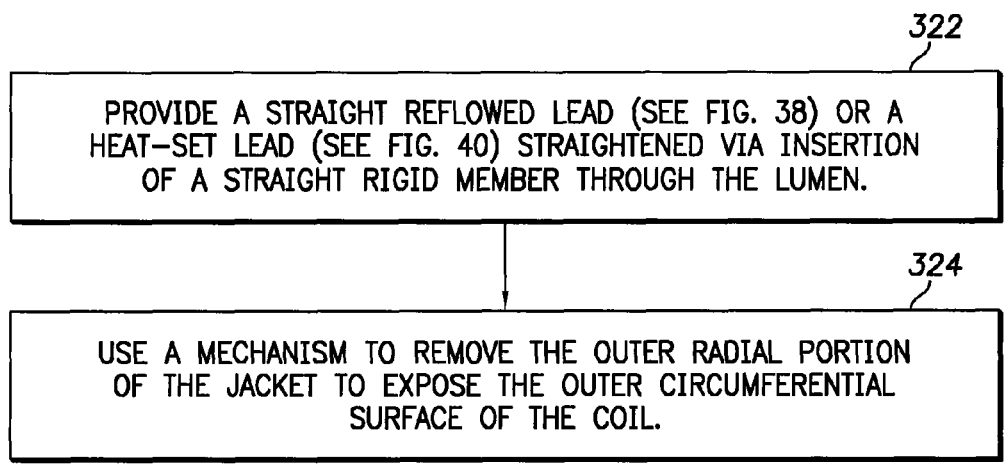
FIG. 47 is a diagram outlining the lead assembly processes illustrated in FIGS. 42-44.

For a discussion of a method of manufacturing the lead 10 discussed above with respect to FIGS. 28, 37 and 41, reference is made to FIGS. 29-47. FIGS. 29-44 illustrate the various states of the lead 10 during its assembly and FIGS. 45-47 are diagrams outlining the assembly process.

Figure 29:
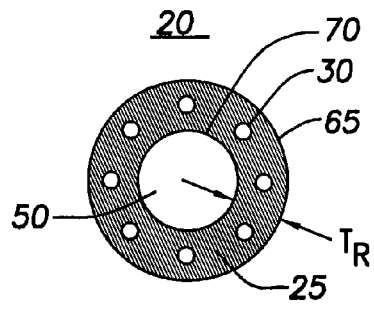
FIGS. 29-30 illustrate the lead core in transverse cross-section wherein the core is provided and then pulled over a mandrel.
Figure 45:
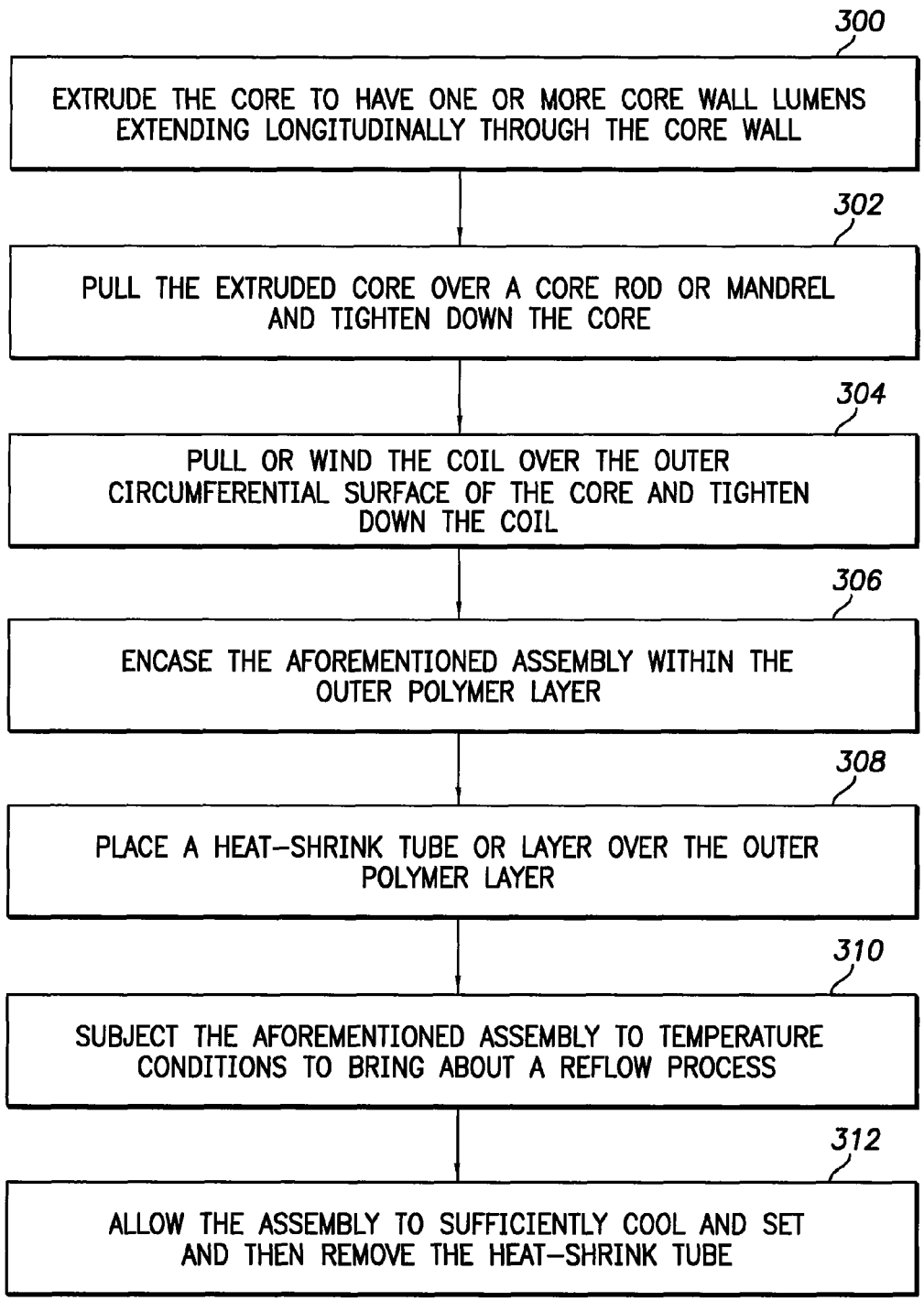
FIG. 45 is a diagram outlining the lead assembly processes illustrated in FIGS. 29-38.

As depicted in FIG. 29, in one embodiment, the core 20 is extruded from a thermoset material, which is thermally stable during the reflow process (FIG. 45, block 300). In one embodiment, the thermoset material comprises PTFE, ePTFE, or silicone rubber. As the core 20 is extruded, a circumferentially continuous core wall 25 may be formed. The inner circumferential surface 70 of the core wall 25 may define the central lumen 50.

As illustrated, in one embodiment, the radial thickness $T_R$ of the core wall 25 may be generally constant about the circumference of the core wall. However, it should be understood that either or both of the outer and inner circumferential surfaces 65, 70 of the core wall 25 may be non-circular and that the radial thickness $T_R$ of the core wall may vary about the circumference of the core wall.

Regardless of whether the radial thickness $T_R$ of the core wall 25 is constant or not, the radial thickness $T_R$, in at least one location, may be sufficient to receive one or more core wall lumens 30 longitudinally extending through the radial thickness $T_R$ of the core wall between the outer and inner circumferential surfaces 65, 70. As depicted in FIG. 29, in one embodiment, the core wall lumens 30 may be evenly radially distributed or arrayed about the ring formed by a lateral cross-section of the core wall 25. However, as indicated in FIG. 14A, it should be understood that the core wall lumens 30 may be unevenly distributed about the circumference of the core wall 25 and may be located at different radiuses from the longitudinal axis of the implantable lead 10. Regardless of the distribution pattern of the core wall lumens 30, the core wall lumens may be integrally formed in the core wall 25 during the extrusion process.

In some embodiments, the wall lumens 30 will have an arcuately extended shape such as depicted in FIG. 16B. In some embodiments, the wall lumens 30 of the core 20 will radially protrude from the outer circumferential surface of the core 20 such as the wall lumens depicted in FIGS. 19A, 19B and 23. In some embodiments, the wall lumens will be replaced with open channels such as those depicted in FIGS. 20A-21B.

In one embodiment, the core 20 is extruded from PTFE, which offers excellent thermal qualities and mechanical stability. Because of the radial thickness $T_R$ of the core walls 25 and the qualities of PTFE, the core wall lumens 30 may not collapse when the core 20 is extruded or subjected to the reflow process, discussed below.

Figure 30:
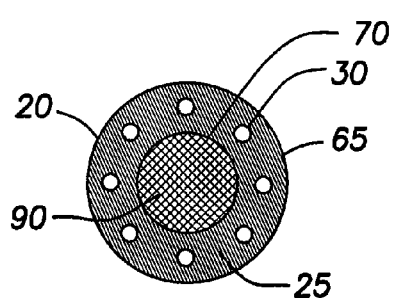

As indicated in FIG. 30, the extruded core 20 may be pulled over a core rod or mandrel 90 and tightened down or otherwise secured (FIG. 45, block 302). The mandrel 90 may support the core 20 during manufacture of the lead 10, for example, in case the diameter of the central lumen 50 is too large to self-support, for example, during reflow. It should be understood that the mandrel 90 may be situated within the core 20 in any suitable manner, for example, by pushing the mandrel into the core or extruding the core over the mandrel.

Figure 31:
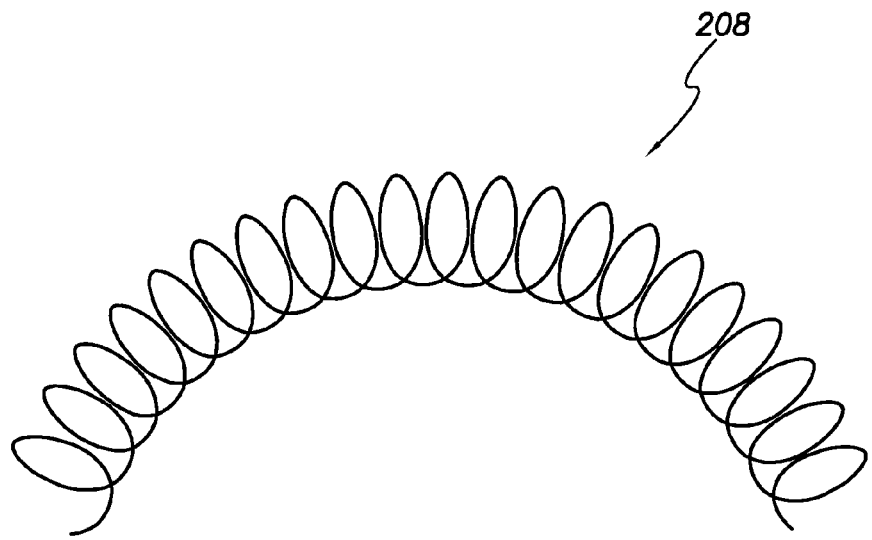
FIG. 31 is an isometric view of a coil biased to assume curved configuration.

As shown in FIG. 31 a coil 208 is provided. Where it is desired for the coil 208 to assist in biasing a portion of the lead 10 into a pre-shaped bend 206, the coil 208 may be preformed such that it biases into a curved configuration. In other embodiments, the coil 208 will not assist forming a pre-shaped bend 206 and, accordingly, will be generally linear such that the coil 208 does not bias into a curved configuration.

In embodiments where the coil 208 does not serve as an electrode 202, but simply assists in curvedly biasing the lead to form a pre-shaped bend 206, the coil 208 will be formed from a material such as MP35NLT, NiTi, or other heat-settable bio-stable materials. In embodiments where the coil 208 serves as an electrode 202 and, in some cases, also as biasing mechanism, the coil 208 will be formed of a material such as Pt/Ir 90/10 alloy or other similar electrically conductive materials.

Figure 32:
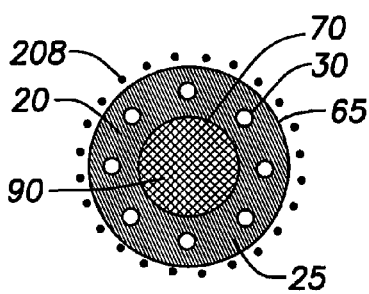

As illustrated in FIG. 32, the coil 208, which may be a helically wound coil having multiple cylindrical or flat filars, may be pulled or wound over the outer circumferential surface 65 of the core 20 and tightened down or otherwise secured (FIG. 45, block 304). While a helically wound coil 208 having multiple filars may be preferred in some embodiments, other coil configurations are possible.

Figure 33:
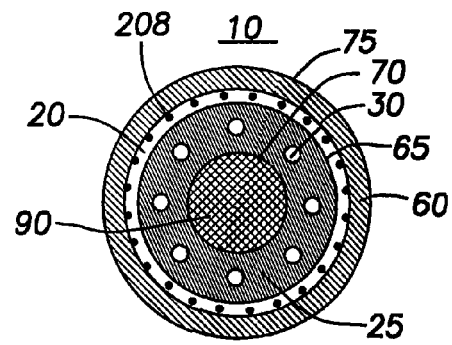
FIGS. 32-34 illustrate the lead in transverse cross-section wherein the coil is placed over the core, the outer jacket is placed over the coil, and the heat-shrink tube is placed over the jacket.

As shown in FIG. 33, the entirety of the aforementioned components may then be surrounded by the outer jacket 60 (FIG. 45, block 306). For example, in one embodiment, the outer jacket 60 comprises an extruded polymer material that is pulled over or otherwise positioned around the aforementioned components and tightened down or otherwise secured. In another embodiment, the outer jacket 60 is extruded over the aforementioned components or, alternatively, extruded and then pulled over the aforementioned components. In one embodiment, the outer jacket 60 comprises a polymer material such as polyurethane (e.g., pellathane 55D), OPTIM®, PIBS, CARBOSIL™, etc. In one embodiment, the outer jacket 60 comprises a polymer material having a durometer value of between approximately 25 Shore A hardness to approximately 55 Shore D hardness. The material of the outer jacket 60 may be selected based on flex-fatigue endurance, abrasion resistance, stiffness, resistance to corrosion, column strength, resistance to metal ion oxidation (MIO), resistance to environmental stress cracking (ESC), etc.

Figure 34:
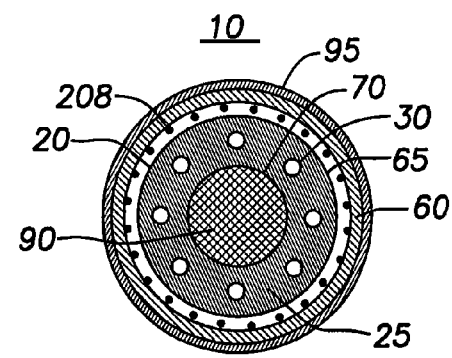
Figure 35:
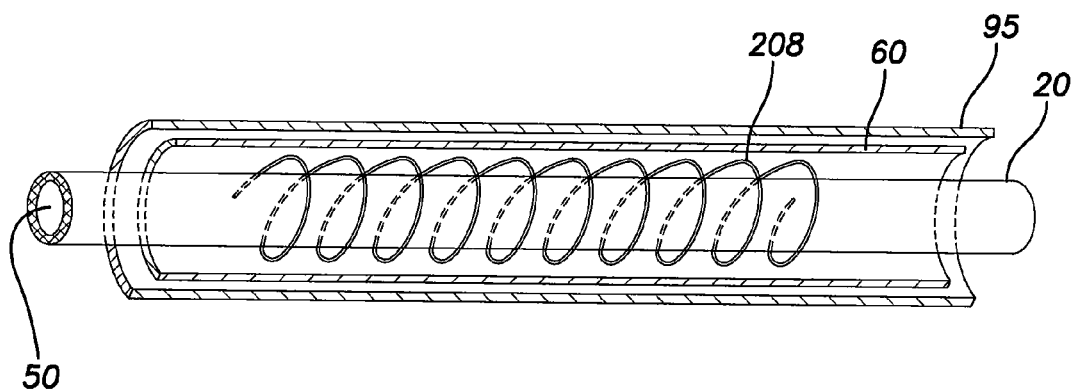
FIG. 35 is an isometric view of a longitudinal segment of the lead in the same state depicted in FIG. 34, wherein the coil, outer jacket and heat-shrink tube extend about the core and the jacket and tube are shown as longitudinal cross sections.

As depicted in FIGS. 34 and 35, a heat-shrink tube or layer 95 may be placed over the outer jacket 60 (FIG. 45, block 308). In one embodiment, the heat-shrink tube 95 comprises a polymeric material, such as FEP (fluorinated ethylene propylene). In one embodiment, the heat-shrink tube 95 may include a shrink temperature ranging from approximately 350 degrees Fahrenheit to approximately 450 degrees Fahrenheit. In any case, it should be understood that the heat-shrink tube 95 should have a shrink temperature that is compatible with a reflow temperature of the material of the jacket 60, as discussed below. Similarly, the material of the core 20 should have a melt temperature that is higher than the reflow temperature of the material of the jacket 60 to avoid melting or softening the core to a point of deformation, which may undesirably alter a desired shape of the core, close lumens and/or allow components to shift position.

The assemblies depicted in FIGS. 34 and 35 may be subjected to heating to a sufficient temperature, such as to the aforementioned temperature conditions, to achieve shrinking of the heat-shrink tube 95 and reflow of the material of the jacket 60 (FIG. 45, block 310). The jacket 60, in turn will melt, encase or encapsulate the coil 208 in the locations where present, and consolidate with the outer circumferential surface 65 of the core 20.

By consolidating, the material of the jacket 60 bonds to the core 20, either by chemical interaction, molecular interaction, simple compression or physical engagement. In particular, any known or hereafter developed primer or surface treatment may be used to enhance the bonding. For example, the core 20 may be formed of PTFE and chemically etched on the outer circumferential surface 65.

In one embodiment, the materials of the core 20 and the outer jacket 60 are chemically compatible such that they can be thermally bonded at the interfaces between the materials. In another embodiment, where the various polymeric materials are not necessarily chemically compatible such that they will thermally bond, the interfacing surfaces of the various materials may be subjected to physical or chemical surface modification to achieve reliable surface bonding. Physical surface modification may include plasma, corona, and laser surface treatments. Chemical surface modification may include chemical etching methods. However, it should be understood that outright chemical compatibility between the various materials or surface modification may not be necessary for reliable bonding into an integral structure.

When heat is applied, shrinking of the heat-shrink tube 95 may generate pressure on the outer jacket 60. Further, the heat-shrink tube 95 may transfer thermal energy to liquefy the outer jacket 60.

To ensure that the outer jacket 60 is completely liquefied during the reflow process, the shrink temperature of the heat-shrink tube 95 may be higher than the softening or melting temperature of the outer jacket 60. The combination of heat and pressure during the reflow process may result in an integral implantable lead 10, for example, via melt flow of the material of the jacket 60 and bonding to the core 20 and possibly the other lead components.

Figure 36:
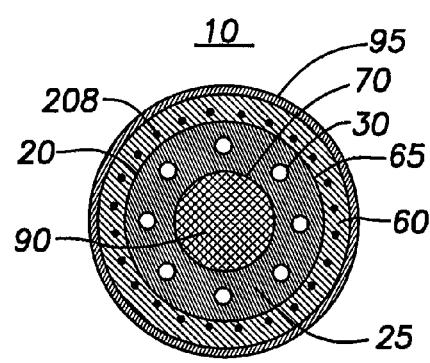
FIG. 36 illustrates the lead in transverse cross-section after the heat-shrink process has caused the outer jacket to bond to the core and impregnate the coil.

Once the reflow process is complete, the assembly appears as depicted in FIG. 36. Once the implantable lead 10 is sufficiently cooled and set, the heat-shrink tube 95 may be removed from the implantable lead 10 (FIG. 45, block 312). The implantable lead 10 then appears as shown in FIGS. 37 and 38.

Once the reflow process, including cooling, is completed, various lead components (e.g., conductor wires 85, etc.) may be inserted into their respective core wall lumens 30. Alternatively, various lead components may be included prior to the reflow process. For example, conductor wires 85 may be routed through the core wall lumens 30 to connect to the coil 208 when the coil 208 is to serve as a defibrillation coil 202.

Various other lead components, such as sensing/pacing electrodes 200, may be included prior to the reflow process, thereby allowing such lead components to the encased and/or bonded by the flow of the material of the jacket 60. However, where appropriate or desired, such lead components may be prevented from such bonding, for example, by including a compliant material, such as hydrogel that may fill in around the lead components to avoid bonding of the jacket material to the lead components.

In one embodiment, as can be understood from FIGS. 40 and 41, the coil 208 can be completely embedded within the outer jacket 60 and assists in forming the pre-shaped curve 206 in the lead 10. To generate a lead with such a curve 206, the coil 208 used in the process discussed with respect to FIGS. 29-38 and 45 is biased to assume a curved state, as depicted in FIG. 31. As shown in FIG. 39, once the reflowed lead 10 has reached the state depicted in FIG. 38 (see block 312 of FIG. 45), the coil region of the reflowed lead 10 can be placed in a curved channel 210 of a forming fixture 212 (block 314 of FIG. 46). The curvature of the curved channel 210 emulates the natural curvature of the coil 208 prior to the coil 208 being placed about the core 20.

The reflowed lead 10 is then heat-set as it resides in the curved channel 210 of the forming fixture 212 (block 316 of FIG. 46). Heat-setting causes the material forming the jacket 60 (e.g., Optim®) to re-set into the shape of the curved channel 210. The curvature provided by the heat-set jacket 60 and the coil 208 combine to provide the curvature in the lead 10 necessary to form the pre-shaped bend 206.

The heat-set lead 10 is allowed to cool in the curved channel 210 (block 318 of FIG. 46). Once the heat-set lead 10 is fully cooled and the jacket 60 and coil 208 fully set, the lead 10 is removed from the channel 210 (block 320 of FIG. 46). The lead 10 now has a pre-shaped bend 206 defined therein as depicted in FIGS. 40 and 41. Insertion of a stylet or guidewire through the lead lumen 50 can straighten the lead bend 206 to allow the lead 10 to be negotiated through the vasculature of the patient to the lead implant site. Upon removal of the stylet or guidewire, the lead bend 206 biases into its curved configuration to facilitate passive fixation of the lead 10 at the implantation site.

In some embodiments, as illustrated in FIG. 28, the coil 208 will be exposed to such that it can serve as a defibrillation coil 202, in addition to assisting in forming the lead bend 206. In other embodiments, the exposed coil 208 will not be located in a lead bend region of the lead 10, but will simply act as a defibrillation coil 202.

To cause the coil 208 to be sufficiently exposed to serve as a defibrillation coil 202 in a region of the lead that is not part of a pre-shaped bend 206, a lead 10 is first provided which has been produced according to the process discussed with respect to FIGS. 29-38 and 45. To cause the coil 208 to be sufficiently exposed to serve as a defibrillation coil 202 in a region of the lead that is part of a pre-shaped bend 206, a lead 10 is first provided which has been produced according to the process discussed with respect to FIGS. 29-38 and 45 and the process discussed with respect to 39-41 and 46. Thus, a straight reflowed lead 10, as depicted in FIG. 38, is provided, or a heat-set lead 10, as depicted in FIG. 40, is provided and straightened via insertion of a straight rigid member through the lumen 50 (block 322 of FIG. 47).

Figure 42:
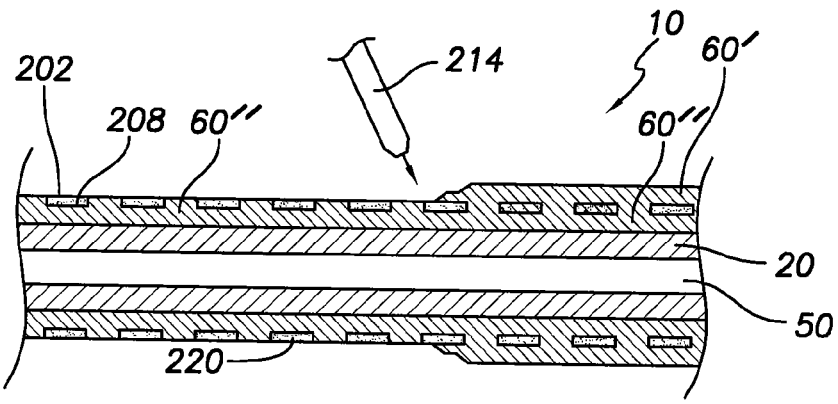
FIG. 42 is a longitudinal cross-section of the lead, wherein a device is being used to remove an outer layer of the outer jacket to reveal the outer surface of the coil so the coil can serve as a defibrillation coil.

As can be understood from FIG. 42, in one embodiment, a mechanism 214 is used to remove the outer radial portion 60' of the jacket 60 to expose the outer circumferential surface of the coil 208 and leave behind an inner radial portion 60" of the jacket 60 (block 324 of FIG. 47). In one embodiment, the mechanism 214 for removing the outer radial portion of the jacket 60 is a mechanical method such as grit-blasting, grinding, turning, etc. In other embodiments, non-mechanical methods such as laser ablation are used to remove the outer radial portion of the jacket 60. In yet other embodiments, the lead 10 will be reflowed to expose the outer circumferential surface of the coil 208.

Figure 43:
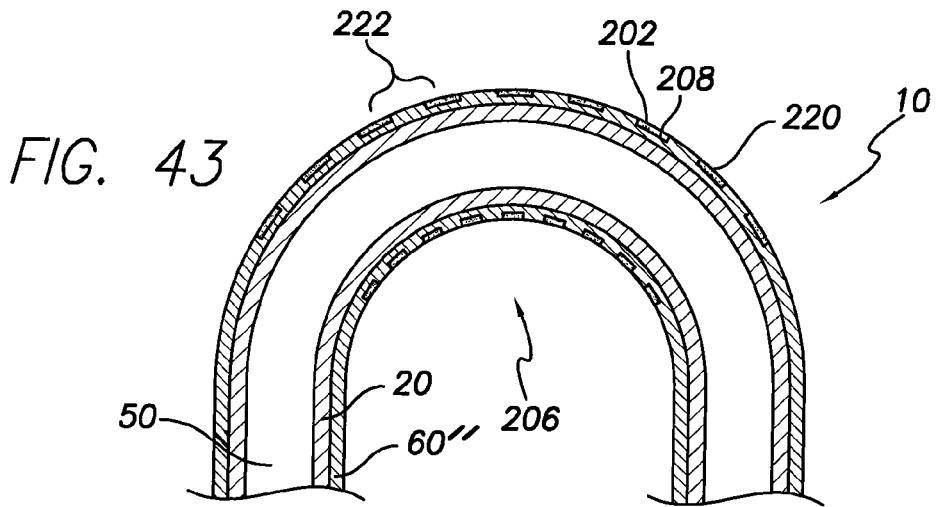
FIG. 43 is a longitudinal cross-section of the lead in the vicinity of the defibrillation coil, wherein the coil also assists in providing the curvature for a pre-shaped bend in the lead.
Figure 44:
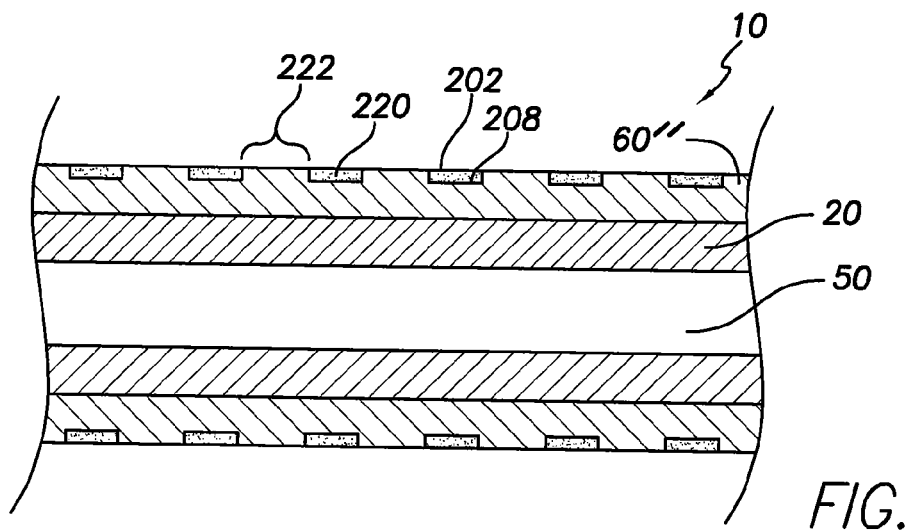
FIG. 44 is a longitudinal cross-section of the lead in the vicinity of the defibrillation coil, wherein the coil does not assist in providing the curvature for a pre-shaped bend in the lead.

As can be understood from FIG. 43, wherein the coil 208 assists in forming the lead bend 206, and FIG. 44, wherein the coil 208 is located in a non-bend region of the lead, the outer circumferential surfaces 220 of the filars of the coil 208 are exposed such that the coil 208 can act as a defibrillation coil 202. The remaining layer 60" of the outer jacket 60 still fills in the spaces 222 between the filars of the coil 208, thereby preventing risk of tissue ingrowth into the coil 208. In one embodiment, the resulting lead 10 is generally isodiametric, wherein the outer circumferential surfaces of the jacket 60 and coil 208 combine to form the outer circumferential surface of the lead 10.

As shown in FIGS. 43 and 44, the filars of the coil 208 can be flat. However, in other embodiments, the filars of the coil 208 will have circular cross-sections as depicted in FIG. 39.

As shown in FIG. 28, some leads 10 will have multiple pre-shaped bends 206. The coils 208 for such leads 10, whether serving as defibrillation coils 202 and bend making mechanisms or solely as bend making mechanisms, can differ from each other with respect to stiffness. This allows the stiffness of the leads 10 at various locations along the length of the leads 10 to be customized or designed for specific requirements. For instance, in one embodiment, a stiffer proximal coil 208" can be used to provide better stability, and a less stiff distal coil 208' can be used to make the lead distal end less traumatic, while still allowing the distal bend 206 to contribute to the overall stability of the lead when implanted. In one embodiment, the difference in coil stiffness is achieved by using different filarities for the two coils 208', 208" and/or subjecting the two coils 208', 208" to different heat treatments. The difference in filarities can be the result of filar pitch, filar number, filar diameter, filar geometry, filar material, etc.

The lead 10 and method of manufacture discussed with respect to FIGS. 28-47 is applicable for all types of leads, including right ventricle leads, right atrium leads, left ventricle leads, etc. While the lead 10 and method discussed with respect to FIGS. 28-47 are advantageous in that they are cost effective to manufacture and result in a reliable configuration, the lead 10 used as a LV lead 10 offers additional benefits. For example, conventional defibrillation therapy is typically delivered using a dual current pathway where energy is distributed from a defibrillation electrode placed on a lead in the right ventricle ("RV") to an electrode in the superior vena cava ("SVC"), and simultaneously, to the metal body of the can of an ICD. Numerous studies indicate that such RV defibrillation/lead systems result in weak shock field intensity in the myocardium of the left ventricle ("LV"). Defibrillation thresholds ("DFTs") can be substantially reduced if electric field strength to the LV is increased.

A variety of concepts involving subcutaneous patches, active pulse generator cans, electrode arrays, and coils placed in the coronary sinus ("CS") have been clinically investigated with moderate success (approximately 20-30% reduction in DFTs). Sequential shock schemes are also found to produce lower DFTs. However, some clinical and animal studies have shown that substantial reduction in DFTs was achievable by placing a small epicardial patch over the LV free wall, along with a sequential shock wave form. While DFTs are reduced by a significant 45% in this configuration, the system was deemed clinically unacceptable due to the need for a transthoracic patch insertion.

Accordingly, there is a well-established clinical advantage for placing defibrillation electrodes over the LV free wall. Furthermore, heart failure patients already receiving a transvenous LV lead for delivery of CRT could further benefit from lower DFTs from the same LV lead. The LV lead 10 discussed with respect to FIGS. 28-47 allows these needs to be met. Specifically, the LV lead 10 and method of manufacturing such a lead provides an easy method for adding a defibrillation coil/electrode on a transvenous LV lead that is typically used in bi-ventricular pacing therapy for patients suffering from heart failure. The LV lead 10 enables bi-ventricular defibrillation therapy resulting in lower DFTs, higher electric field strength to the LV, and in doing so, a reduction in the maximum energy requirement and size of the ICD device, as well as an increase in the longevity of the device.

Additionally, the pre-curved coil 208 used to manufacture the pre-bend 206 equipped leads 10 provides a passive fixation curve to the lead. The pre-curved coil 208 is advantageous in that it assists in establishing a pre-bend curve 206 in a lead 10 having a core 20 containing materials, such as PTFE, that are inherently averse to having shapes permanently set into them.

Although the present invention has been described with reference to preferred embodiments, persons skilled in the art will recognize that changes may be made in form and detail without departing from the spirit and scope of the invention. For example, a first reflow of the jacket may bond the jacket to the core, followed by assembly of lead component over the jacket and a second reflow of the jacket to consolidate the assembly.

What is claimed is:

1. A method of manufacturing an implantable lead, the method comprising:
   providing a core including at least one longitudinal lumen;
   providing a first coil having a first filarity about an outer circumferential surface of a first portion of the core;
   providing a second coil having a second filarity different from the first filarity, about an outer circumferential surface of a second portion of the core longitudinally spaced from the first portion of the core;
   providing a jacket about an outer circumferential surface of the first and second coils, wherein the jacket is formed of a reflowable material;
   causing the material of the jacket to reflow through the first and second coils and bond to the core; and
   causing the outer circumferential surface of at least one of the first and second coils to be exposed through the jacket.

2. The method of claim 1, wherein causing the material of the jacket to reflow includes applying heat to the material.

3. The method of claim 1, wherein causing the material of the jacket to reflow includes compressing the material.

4. The method of claim 1, wherein causing the material of the jacket to reflow includes subjecting the material to a heat-shrink process.

5. The method of claim 1, further comprising providing a heat-shrink tube about an outer circumferential surface of the jacket and then subjecting the tube to heat.

6. The method of claim 1, further comprising, subsequent to the reflowing of the jacket, causing a region of the lead containing at least one of the first and second coils to assume a curvature and then subjecting the region to a heat-setting process.

7. The method of claim 1, wherein at least one of the first and second coils is biased to assume a pre-shaped curvature prior to being provided about the core.

8. The method of claim 7, further comprising, subsequent to the reflowing of the jacket, causing a region of the lead containing at least one of the first and second coils to assume a curvature and then subjecting the region to a heat-setting process.

9. The method of claim 7, further comprising, subsequent to the reflowing of the jacket, placing a region of the lead containing at least one of the first and second coils within a curved channel of a forming fixture.

10. The method of claim 9, further comprising subjecting the region of the lead containing at least one of the first and second coils to a heat-setting process when residing in the channel.

11. The method of claim 1, wherein causing the outer circumferential surface of at least one of the first and second coils to be exposed includes mechanically removing a layer of the jacket extending over the outer circumferential surface of the at least one of the first and second coils subsequent to the reflow.

12. The method of claim 11, wherein mechanically removing a layer includes employing grit-blasting, grinding or turning.

13. The method of claim 11, wherein causing the outer circumferential surface of at least one of the first and second coils to be exposed includes removing, via laser ablation, a layer of the jacket extending over the outer circumferential surface of the at least one of the first and second coils subsequent to the reflow.

14. The method of claim 1, wherein causing the outer circumferential surface of at least one of the first and second coils to be exposed includes employing a heat-shrink process to remove a layer of the jacket extending over the outer circumferential surface of the at least one of the first and second coils subsequent to the reflow.

15. The method of claim 1, further comprising electrically coupling at least one of the first and second coils to an electrical conductor extending through the core.

16. The method of claim 1, wherein material of the jacket remains between individual filars of the at least one of the first and second coils.

17. The method of claim 1 wherein providing the first coil of the first filarity and the second coil of the second filarity comprises providing a first coil having at one of a filar pitch, filar number, filar diameter, filar geometry and filar material different from that of the second coil.

18. An implantable lead comprising:
a core having at least one lumen extending there through;
a first coil having a first filarity extending about an outer circumferential surface of the core;
a second coil having a second filarity different from the first filarity, extending about an outer circumferential surface of a second portion of the core longitudinally spaced from the first portion of the core; and
a jacket reflowed about the outer circumferential surface of the core and about an outer circumferential surface of the first and second coils and impregnating the first coil and the second coil, wherein the outer circumferential surface of at least one of the first and second coils is exposed through the jacket and jacket material exists between individual filars of the coil.

19. The lead of claim 18, wherein the lead is a transvenous LV lead.

20. The lead of claim 19, wherein the first coil is a defibrillation coil.

21. The lead of claim 18, in which the first coil is in an area of the lead not having a pre-shaped curve.

22. The lead of claim 18, further comprising a pre-shaped bend in the lead, wherein at least one of the first and second coils assists in establishing the pre-shaped bend.

23. The lead of claim 18, wherein jacket material initially covers the outer circumferential surface of the first and second coils and is removed for the outer circumferential surface of the at least one of the first and second coils to expose the at least one of the first and second coils through the jacket.

24. The lead of claim 18, wherein the jacket is extruded over the outer circumferential surface of the first and second coils and jacket material is removed to expose the outer circumferential surface of the at least one of the first and second coils through the jacket.

* * * * *